(12) United States Patent
Hendricksen et al.

(10) Patent No.: US 10,537,321 B2
(45) Date of Patent: *Jan. 21, 2020

(54) SUTURE PASSERS ADAPTED FOR USE IN CONSTRAINED REGIONS

(71) Applicant: Ceterix Orthopaedics, Inc., Fremont, CA (US)

(72) Inventors: Michael J. Hendricksen, Redwood City, CA (US); Michael Murillo, Menlo Park, CA (US); Christopher P. Bender, Oakland, CA (US); Mark Y. Hirotsuka, San Jose, CA (US); Stephen J. Peter, San Francisco, CA (US)

(73) Assignee: Ceterix Orthopaedics, Inc., Fremont, CA (US)

( * ) Notice: Subject to any disclaimer, the term of this patent is extended or adjusted under 35 U.S.C. 154(b) by 89 days.

This patent is subject to a terminal disclaimer.

(21) Appl. No.: 14/681,528

(22) Filed: Apr. 8, 2015

(65) Prior Publication Data

US 2015/0297215 A1 Oct. 22, 2015
US 2019/0274673 A2 Sep. 12, 2019

Related U.S. Application Data

(60) Provisional application No. 61/976,742, filed on Apr. 8, 2014.

(51) Int. Cl.
*A61B 17/04* (2006.01)
(52) U.S. Cl.
CPC ...... *A61B 17/0469* (2013.01); *A61B 17/0485* (2013.01)

(58) Field of Classification Search
CPC ............ A61B 17/0469; A61B 17/0482; A61B 17/062; A61B 17/0625; A61B 17/0483;
(Continued)

(56) References Cited

U.S. PATENT DOCUMENTS

| 1,037,864 A | 9/1912 | Carlson et al. |
| 2,738,790 A | 3/1956 | Todt, Sr. et al. |

(Continued)

FOREIGN PATENT DOCUMENTS

| CN | 201263696 Y | 7/2009 |
| CN | 101961256 A | 2/2011 |

(Continued)

OTHER PUBLICATIONS

Murillo et al.; U.S. Appl. No. 14/572,485 entitled "Automatically reloading suture passer devices and methods," filed Dec. 16, 2014.

(Continued)

*Primary Examiner* — Katherine H Schwiker
(74) *Attorney, Agent, or Firm* — Norman F. Hainer, Jr.

(57) ABSTRACT

Described herein suture passer apparatus (devices and systems) that may be used to suture tissue within a narrow, confined space. In particular, described herein are suture passers having an elongate body and a lower jaw member that houses a tissue penetrator that is adapted to extend laterally from the lower jaw member and be deflected by a second jaw member? The second jaw member typically deflects the tissue penetrator either distally or proximally.

11 Claims, 22 Drawing Sheets

(58) Field of Classification Search
CPC . A61B 17/0491; A61B 17/29; A61B 17/0485; A61B 2017/047; A61B 2017/06042; A61B 2017/2926; A61B 2017/06052; A61B 17/0472; A61B 17/0474; A61B 17/0475; A61B 17/0477; A61B 17/0479; A61B 17/048; A61B 2017/00371; A61B 2017/06047; A61B 2017/0646
See application file for complete search history.

(56) References Cited

U.S. PATENT DOCUMENTS

| | | |
|---|---|---|
| 2,748,773 A | 6/1956 | Vacheresse, Jr. |
| 3,470,875 A | 10/1969 | Johnson |
| 3,580,256 A | 5/1971 | Wilkinson et al. |
| 3,807,407 A | 4/1974 | Schweizer |
| 3,842,840 A | 10/1974 | Schweizer |
| 3,901,244 A | 8/1975 | Schweizer |
| 4,021,896 A | 5/1977 | Stierlein |
| 4,109,658 A | 8/1978 | Hughes |
| 4,164,225 A | 8/1979 | Johnson et al. |
| 4,236,470 A | 12/1980 | Stenson |
| 4,345,601 A | 8/1982 | Fukuda |
| 4,440,171 A | 4/1984 | Nomoto et al. |
| 4,553,543 A | 11/1985 | Amarasinghe |
| 4,605,002 A | 8/1986 | Rebuffat |
| 4,706,666 A | 11/1987 | Sheets |
| 4,836,205 A | 6/1989 | Barrett |
| 4,957,498 A | 9/1990 | Caspari et al. |
| 4,981,149 A | 1/1991 | Yoon et al. |
| 5,002,561 A | 3/1991 | Fisher |
| 5,011,491 A | 4/1991 | Boenko et al. |
| 5,037,433 A | 8/1991 | Wilk et al. |
| 5,059,201 A | 10/1991 | Asnis |
| 5,059,206 A | 10/1991 | Winters |
| 5,112,344 A | 5/1992 | Petros |
| 5,129,912 A | 7/1992 | Noda et al. |
| 5,139,520 A | 8/1992 | Rosenberg |
| 5,156,608 A | 10/1992 | Troidl et al. |
| 5,193,473 A | 3/1993 | Asao et al. |
| 5,219,358 A | 6/1993 | Bendel et al. |
| 5,222,962 A | 6/1993 | Burkhart |
| 5,250,053 A | 10/1993 | Snyder |
| 5,250,055 A | 10/1993 | Moore et al. |
| 5,281,237 A | 1/1994 | Gimpelson |
| 5,312,422 A | 5/1994 | Trott |
| 5,320,633 A | 6/1994 | Allen et al. |
| 5,330,488 A | 7/1994 | Goldrath |
| 5,336,229 A | 8/1994 | Noda |
| 5,342,389 A | 8/1994 | Haber et al. |
| 5,364,410 A | 11/1994 | Failla et al. |
| 5,368,601 A | 11/1994 | Sauer et al. |
| 5,383,877 A | 1/1995 | Clarke |
| 5,389,103 A | 2/1995 | Melzer et al. |
| 5,391,174 A | 2/1995 | Weston |
| 5,397,325 A | 3/1995 | Della Badia et al. |
| 5,403,328 A | 4/1995 | Shallman |
| 5,405,352 A | 4/1995 | Weston |
| 5,405,532 A | 4/1995 | Loew et al. |
| 5,431,666 A | 7/1995 | Sauer et al. |
| 5,431,669 A | 7/1995 | Thompson et al. |
| 5,437,681 A | 8/1995 | Meade et al. |
| 5,454,823 A | 10/1995 | Richardson et al. |
| 5,454,834 A | 10/1995 | Boebel et al. |
| 5,468,251 A | 11/1995 | Buelna |
| 5,474,057 A | 12/1995 | Makower et al. |
| 5,478,344 A | 12/1995 | Stone et al. |
| 5,478,345 A | 12/1995 | Stone et al. |
| 5,480,406 A | 1/1996 | Nolan et al. |
| 5,496,335 A | 3/1996 | Thomason et al. |
| 5,499,991 A | 3/1996 | Garman et al. |
| 5,507,756 A | 4/1996 | Hasson |
| 5,507,757 A | 4/1996 | Sauer et al. |
| 5,520,702 A | 5/1996 | Sauer et al. |
| 5,540,704 A | 7/1996 | Gordon et al. |
| 5,540,705 A | 7/1996 | Meade et al. |
| 5,562,686 A | 10/1996 | Sauer et al. |
| 5,569,301 A | 10/1996 | Granger et al. |
| 5,571,090 A | 11/1996 | Sherts |
| 5,571,119 A | 11/1996 | Atala |
| 5,575,800 A | 11/1996 | Gordon |
| 5,578,044 A | 11/1996 | Gordon et al. |
| 5,601,576 A | 2/1997 | Garrison |
| 5,607,435 A | 3/1997 | Sachdeva et al. |
| 5,616,131 A | 4/1997 | Sauer et al. |
| 5,618,290 A | 4/1997 | Toy et al. |
| 5,626,588 A | 5/1997 | Sauer et al. |
| 5,632,748 A | 5/1997 | Beck et al. |
| 5,632,751 A | 5/1997 | Piraka |
| 5,643,289 A | 7/1997 | Sauer et al. |
| 5,645,552 A | 7/1997 | Sherts |
| 5,653,716 A | 8/1997 | Malo et al. |
| 5,665,096 A | 9/1997 | Yoon |
| 5,669,917 A | 9/1997 | Sauer et al. |
| 5,674,229 A | 10/1997 | Tovey et al. |
| 5,674,230 A | 10/1997 | Tovey et al. |
| 5,681,331 A | 10/1997 | de la Torre et al. |
| 5,690,652 A | 11/1997 | Wurster et al. |
| 5,713,910 A | 2/1998 | Gordon et al. |
| 5,728,107 A | 3/1998 | Zlock et al. |
| 5,728,113 A | 3/1998 | Sherts |
| 5,730,747 A | 3/1998 | Ek et al. |
| 5,741,278 A | 4/1998 | Stevens |
| 5,749,879 A | 5/1998 | Middleman et al. |
| 5,755,728 A | 5/1998 | Maki |
| 5,759,188 A | 6/1998 | Yoon |
| 5,766,183 A | 6/1998 | Sauer |
| 5,792,153 A | 8/1998 | Swain et al. |
| 5,797,958 A | 8/1998 | Yoon |
| 5,800,445 A | 9/1998 | Ratcliff et al. |
| 5,814,054 A | 9/1998 | Kortenbach et al. |
| 5,814,069 A | 9/1998 | Schulze et al. |
| 5,824,009 A | 10/1998 | Fukuda et al. |
| 5,827,300 A | 10/1998 | Fleega |
| 5,843,126 A | 12/1998 | Jameel |
| 5,865,836 A | 2/1999 | Miller |
| 5,871,490 A | 2/1999 | Schulze et al. |
| 5,876,411 A | 3/1999 | Kontos |
| 5,876,412 A | 3/1999 | Piraka |
| 5,895,393 A | 4/1999 | Pagedas |
| 5,895,395 A | 4/1999 | Yeung |
| 5,897,563 A | 4/1999 | Yoon et al. |
| 5,899,911 A | 5/1999 | Carter |
| 5,906,630 A | 5/1999 | Anderhub et al. |
| 5,908,428 A | 6/1999 | Scirica et al. |
| 5,910,148 A | 6/1999 | Reimels et al. |
| 5,935,138 A | 8/1999 | McJames, II et al. |
| 5,938,668 A | 8/1999 | Scirica et al. |
| 5,944,739 A | 8/1999 | Zlock et al. |
| 5,947,982 A | 9/1999 | Duran |
| 5,980,538 A | 11/1999 | Fuchs et al. |
| 5,993,466 A | 11/1999 | Yoon |
| 5,997,554 A | 12/1999 | Thompson |
| 6,039,753 A | 3/2000 | Meislin |
| 6,042,601 A | 3/2000 | Smith |
| 6,048,351 A | 4/2000 | Gordon et al. |
| 6,051,006 A | 4/2000 | Shluzas et al. |
| 6,053,933 A | 4/2000 | Balazs et al. |
| 6,056,771 A | 5/2000 | Proto |
| 6,071,289 A | 6/2000 | Stefanchik et al. |
| 6,077,276 A | 6/2000 | Kontos |
| 6,099,550 A | 8/2000 | Yoon |
| 6,099,568 A | 8/2000 | Simonian et al. |
| 6,113,610 A | 9/2000 | Poncet |
| 6,126,666 A | 10/2000 | Trapp et al. |
| 6,129,741 A | 10/2000 | Wurster et al. |
| 6,139,556 A | 10/2000 | Kontos |
| 6,152,934 A | 11/2000 | Harper et al. |
| 6,159,224 A | 12/2000 | Yoon |
| 6,190,396 B1 | 2/2001 | Whitin et al. |
| 6,221,085 B1 | 4/2001 | Djurovic |
| 6,231,606 B1 | 5/2001 | Graf et al. |
| 6,238,414 B1 | 5/2001 | Griffiths |
| 6,264,694 B1 | 7/2001 | Weiler |

(56) References Cited

U.S. PATENT DOCUMENTS

| | | |
|---|---|---|
| 6,277,132 B1 | 8/2001 | Brhel |
| 6,322,570 B1 | 11/2001 | Matsutani et al. |
| 6,325,808 B1 | 12/2001 | Bernard et al. |
| 6,355,050 B1 | 3/2002 | Andreas et al. |
| 6,368,334 B1 | 4/2002 | Sauer |
| 6,368,343 B1 | 4/2002 | Bonutti et al. |
| 6,443,963 B1 | 9/2002 | Baldwin et al. |
| 6,511,487 B1 | 1/2003 | Oren et al. |
| 6,533,795 B1 | 3/2003 | Tran et al. |
| 6,533,796 B1 | 3/2003 | Sauer et al. |
| 6,551,330 B1 | 4/2003 | Bain et al. |
| 6,585,744 B1 | 7/2003 | Griffith |
| 6,626,917 B1 | 9/2003 | Craig |
| 6,626,929 B1 | 9/2003 | Bannerman |
| 6,638,283 B2 | 10/2003 | Thal |
| 6,638,286 B1 | 10/2003 | Burbank et al. |
| 6,641,592 B1 | 11/2003 | Sauer et al. |
| 6,719,765 B2 | 4/2004 | Bonutti |
| 6,723,107 B1 | 4/2004 | Skiba et al. |
| 6,770,084 B1 | 8/2004 | Bain et al. |
| 6,833,005 B1 | 12/2004 | Mantas |
| 6,896,686 B2 | 5/2005 | Weber |
| 6,921,408 B2 | 7/2005 | Sauer |
| 6,923,806 B2 | 8/2005 | Hooven et al. |
| 6,923,819 B2 | 8/2005 | Meade et al. |
| 6,936,054 B2 | 8/2005 | Chu |
| 6,972,027 B2 | 12/2005 | Fallin et al. |
| 6,984,237 B2 | 1/2006 | Hatch et al. |
| 6,991,635 B2 | 1/2006 | Takamoto et al. |
| 6,997,931 B2 | 2/2006 | Sauer et al. |
| 6,997,932 B2 | 2/2006 | Dreyfuss et al. |
| 7,004,951 B2 | 2/2006 | Gibbens, III |
| 7,029,480 B2 | 4/2006 | Klein et al. |
| 7,029,481 B1 | 4/2006 | Burdulis, Jr. et al. |
| 7,041,111 B2 | 5/2006 | Chu |
| 7,063,710 B2 | 6/2006 | Takamoto et al. |
| 7,087,060 B2 | 8/2006 | Clark |
| 7,112,208 B2 | 9/2006 | Morris et al. |
| 7,118,583 B2 | 10/2006 | O'Quinn et al. |
| 7,131,978 B2 | 11/2006 | Sancoff et al. |
| 7,153,312 B1 | 12/2006 | Torrie et al. |
| 7,166,116 B2 | 1/2007 | Lizardi et al. |
| 7,175,636 B2 | 2/2007 | Yamamoto et al. |
| 7,211,093 B2 | 5/2007 | Sauer et al. |
| 7,232,448 B2 | 6/2007 | Battles et al. |
| 7,235,086 B2 | 6/2007 | Sauer et al. |
| 7,311,715 B2 | 12/2007 | Sauer et al. |
| 7,344,545 B2 | 3/2008 | Takemoto et al. |
| 7,390,328 B2 | 6/2008 | Modesitt |
| 7,481,817 B2 | 1/2009 | Sauer |
| 7,481,826 B2 | 1/2009 | Cichocki |
| 7,491,212 B2 | 2/2009 | Sikora et al. |
| 7,588,583 B2 | 9/2009 | Hamilton et al. |
| 7,594,922 B1 | 9/2009 | Goble et al. |
| 7,632,284 B2 | 12/2009 | Martinek et al. |
| 7,674,276 B2 | 3/2010 | Stone et al. |
| 7,717,927 B2 | 5/2010 | Hahn et al. |
| 7,722,630 B1 * | 5/2010 | Stone ............... A61B 17/0491 606/144 |
| 7,731,727 B2 | 6/2010 | Sauer |
| 7,736,372 B2 | 6/2010 | Reydel et al. |
| 7,749,236 B2 | 7/2010 | Oberlaender et al. |
| 7,842,050 B2 | 11/2010 | Diduch et al. |
| 7,879,046 B2 | 2/2011 | Weinert et al. |
| 7,883,519 B2 | 2/2011 | Oren et al. |
| 7,951,147 B2 | 5/2011 | Privitera et al. |
| 7,951,159 B2 | 5/2011 | Stokes et al. |
| 7,972,344 B2 | 7/2011 | Murray et al. |
| 8,298,230 B2 | 10/2012 | Sutter et al. |
| 8,394,112 B2 | 3/2013 | Nason |
| 8,398,673 B2 | 3/2013 | Hinchliffe et al. |
| 8,449,533 B2 | 5/2013 | Saliman et al. |
| 8,465,505 B2 | 6/2013 | Murino et al. |
| 8,500,809 B2 | 8/2013 | Saliman |
| 8,562,631 B2 | 10/2013 | Saliman |
| 8,632,563 B2 | 1/2014 | Nagase et al. |
| 8,647,354 B2 | 2/2014 | Domingo |
| 8,663,253 B2 | 3/2014 | Saliman |
| 8,702,731 B2 | 4/2014 | Saliman |
| 8,808,299 B2 | 8/2014 | Saliman et al. |
| 8,821,518 B2 | 9/2014 | Saliman |
| 8,888,848 B2 | 11/2014 | Saliman et al. |
| 8,911,456 B2 | 12/2014 | McCutcheon et al. |
| 8,920,441 B2 | 12/2014 | Saliman et al. |
| 9,011,454 B2 | 4/2015 | Hendrickson et al. |
| 2001/0041938 A1 | 11/2001 | Hein |
| 2002/0169477 A1 | 11/2002 | Demopulos et al. |
| 2003/0023250 A1 | 1/2003 | Watschke et al. |
| 2003/0065336 A1 | 4/2003 | Xiao |
| 2003/0065337 A1 | 4/2003 | Topper et al. |
| 2003/0078599 A1 | 4/2003 | O'Quinn et al. |
| 2003/0078617 A1 | 4/2003 | Schwartz et al. |
| 2003/0181926 A1 | 9/2003 | Dana et al. |
| 2003/0204194 A1 | 10/2003 | Bittar |
| 2003/0216755 A1 | 11/2003 | Shikhman et al. |
| 2003/0233106 A1 | 12/2003 | Dreyfuss |
| 2004/0117014 A1 | 6/2004 | Bryant |
| 2004/0249392 A1 | 12/2004 | Mikkaichi et al. |
| 2004/0249394 A1 | 12/2004 | Morris et al. |
| 2004/0267304 A1 | 12/2004 | Zannis et al. |
| 2005/0033319 A1 | 2/2005 | Gambale et al. |
| 2005/0033365 A1 | 2/2005 | Courage |
| 2005/0043746 A1 | 2/2005 | Pollak et al. |
| 2005/0080434 A1 | 4/2005 | Chung et al. |
| 2005/0090837 A1 | 4/2005 | Sixto, Jr. et al. |
| 2005/0090840 A1 | 4/2005 | Gerbino et al. |
| 2005/0154403 A1 | 7/2005 | Sauer et al. |
| 2005/0228406 A1 | 10/2005 | Bose |
| 2005/0288690 A1 | 12/2005 | Bourque et al. |
| 2006/0020272 A1 | 1/2006 | Gildenberg |
| 2006/0047289 A1 | 3/2006 | Fogel |
| 2006/0084974 A1 | 4/2006 | Privitera et al. |
| 2006/0178680 A1 | 8/2006 | Beverly et al. |
| 2006/0282098 A1 | 12/2006 | Shelton et al. |
| 2007/0032799 A1 | 2/2007 | Pantages et al. |
| 2007/0038230 A1 | 2/2007 | Stone et al. |
| 2007/0156174 A1 | 7/2007 | Kaiser et al. |
| 2007/0185532 A1 | 8/2007 | Stone et al. |
| 2007/0219571 A1 | 9/2007 | Balbierz et al. |
| 2007/0250118 A1 | 10/2007 | Masini |
| 2007/0260260 A1 | 11/2007 | Hahn et al. |
| 2007/0260278 A1 | 11/2007 | Wheeler et al. |
| 2008/0086147 A1 | 4/2008 | Knapp |
| 2008/0091219 A1 | 4/2008 | Marshall et al. |
| 2008/0097482 A1 | 4/2008 | Bain et al. |
| 2008/0097489 A1 | 4/2008 | Goldfarb et al. |
| 2008/0140091 A1 | 6/2008 | DeDeyne et al. |
| 2008/0140094 A1 | 6/2008 | Schwartz et al. |
| 2008/0228204 A1 | 9/2008 | Hamilton et al. |
| 2008/0234725 A1 | 9/2008 | Griffiths et al. |
| 2008/0243147 A1 | 10/2008 | Hamilton et al. |
| 2008/0269783 A1 | 10/2008 | Griffith |
| 2008/0275553 A1 | 11/2008 | Wolf et al. |
| 2008/0294256 A1 | 11/2008 | Hagan et al. |
| 2009/0012520 A1 | 1/2009 | Hixson et al. |
| 2009/0012538 A1 | 1/2009 | Saliman |
| 2009/0018554 A1 | 1/2009 | Thorne et al. |
| 2009/0062816 A1 | 3/2009 | Weber |
| 2009/0062819 A1 | 3/2009 | Burkhart et al. |
| 2009/0105729 A1 | 4/2009 | Zentgraf |
| 2009/0105751 A1 | 4/2009 | Zentgraf |
| 2009/0112232 A1 | 4/2009 | Crainich et al. |
| 2009/0131956 A1 | 5/2009 | Dewey et al. |
| 2009/0209998 A1 | 8/2009 | Widmann |
| 2009/0216268 A1 | 8/2009 | Panter |
| 2009/0228041 A1 | 9/2009 | Domingo |
| 2009/0259233 A1 | 10/2009 | Bogart et al. |
| 2009/0281619 A1 | 11/2009 | Le et al. |
| 2009/0306684 A1 | 12/2009 | Stone et al. |
| 2009/0306776 A1 | 12/2009 | Murray |
| 2010/0057109 A1 | 3/2010 | Clerc et al. |
| 2010/0106169 A1 | 4/2010 | Niese et al. |
| 2010/0114137 A1 | 5/2010 | Vidal et al. |
| 2010/0121352 A1 | 5/2010 | Murray et al. |

(56) References Cited

U.S. PATENT DOCUMENTS

| | | |
|---|---|---|
| 2010/0130990 A1 | 5/2010 | Saliman |
| 2010/0145364 A1 | 6/2010 | Keren et al. |
| 2010/0185232 A1 | 7/2010 | Hughett et al. |
| 2010/0198235 A1 | 8/2010 | Pierce et al. |
| 2010/0217286 A1 | 8/2010 | Gerber et al. |
| 2010/0228271 A1 | 9/2010 | Marshall et al. |
| 2010/0241142 A1 | 9/2010 | Akyuz et al. |
| 2010/0249809 A1 | 9/2010 | Singhatat et al. |
| 2010/0280530 A1 | 11/2010 | Hashiba |
| 2010/0305581 A1 | 12/2010 | Hart |
| 2010/0305583 A1 | 12/2010 | Baird et al. |
| 2011/0022061 A1 | 1/2011 | Orphanos et al. |
| 2011/0022063 A1 | 1/2011 | McClurg et al. |
| 2011/0028998 A1 | 2/2011 | Adams et al. |
| 2011/0060350 A1 | 3/2011 | Powers et al. |
| 2011/0071563 A1 | 3/2011 | Magliani |
| 2011/0087246 A1 | 4/2011 | Saliman et al. |
| 2011/0100173 A1 | 5/2011 | Stone et al. |
| 2011/0112555 A1 | 5/2011 | Overes et al. |
| 2011/0112556 A1* | 5/2011 | Saliman .............. A61B 17/0469 606/145 |
| 2011/0118760 A1 | 5/2011 | Gregoire et al. |
| 2011/0130773 A1 | 6/2011 | Saliman et al. |
| 2011/0152892 A1 | 6/2011 | Saliman et al. |
| 2011/0190815 A1 | 8/2011 | Saliman |
| 2011/0251626 A1 | 10/2011 | Wyman et al. |
| 2011/0270306 A1 | 11/2011 | Denham et al. |
| 2012/0101524 A1 | 4/2012 | Bennett |
| 2012/0283750 A1 | 11/2012 | Saliman et al. |
| 2012/0283753 A1 | 11/2012 | Saliman et al. |
| 2012/0283754 A1* | 11/2012 | Murillo .............. A61B 17/0469 606/145 |
| 2012/0303046 A1 | 11/2012 | Stone et al. |
| 2013/0072948 A1 | 3/2013 | States, III et al. |
| 2013/0085512 A1 | 4/2013 | Wyman et al. |
| 2013/0253536 A1* | 9/2013 | Harris ................ A61B 17/0401 606/139 |
| 2013/0331865 A1 | 12/2013 | Murillo et al. |
| 2014/0074157 A1 | 3/2014 | Hirotsuka et al. |
| 2014/0188136 A1 | 7/2014 | Cournoyer et al. |
| 2014/0222034 A1 | 8/2014 | Saliman |
| 2014/0276981 A1 | 9/2014 | Hendricksen et al. |
| 2014/0276987 A1 | 9/2014 | Saliman |
| 2015/0034694 A1 | 2/2015 | Cappola |
| 2015/0039030 A1 | 2/2015 | Saliman et al. |
| 2015/0073442 A1 | 3/2015 | Saliman et al. |
| 2015/0088163 A1 | 3/2015 | George et al. |
| 2015/0142022 A1 | 5/2015 | George et al. |
| 2015/0157317 A1 | 6/2015 | Bagaoisan et al. |
| 2015/0173742 A1 | 6/2015 | Palese et al. |
| 2015/0173743 A1 | 6/2015 | Palese et al. |
| 2015/0257756 A1 | 9/2015 | Sauer |
| 2018/0303476 A1 | 10/2018 | Murillo et al. |

FOREIGN PATENT DOCUMENTS

| | | |
|---|---|---|
| CN | 103298503 A | 9/2013 |
| CN | 103717149 A | 4/2014 |
| EP | 0647431 A2 | 4/1995 |
| EP | 2030575 A1 | 3/2009 |
| EP | 2184015 A2 | 5/2010 |
| EP | 2081481 B1 | 11/2015 |
| JP | 3032847 U | 3/1991 |
| JP | 2009138029 A | 6/2009 |
| JP | 2009538190 | 11/2009 |
| SU | 376089 A | 4/1973 |
| SU | 728848 A1 | 4/1980 |
| SU | 1725847 A1 | 4/1992 |
| WO | WO 92/05828 A1 | 4/1992 |
| WO | WO 95/13021 A1 | 5/1995 |
| WO | WO98/11825 A1 | 3/1998 |
| WO | WO 98/31288 A1 | 7/1998 |
| WO | WO 99/34744 A1 | 7/1999 |
| WO | WO 99/42036 A1 | 8/1999 |
| WO | WO 99/47050 A2 | 9/1999 |
| WO | WO01/56478 A1 | 8/2001 |
| WO | WO 02/07607 A1 | 1/2002 |
| WO | WO 02/096296 A1 | 12/2002 |
| WO | WO 03/077771 A1 | 9/2003 |
| WO | WO 2006/001040 A1 | 1/2006 |
| WO | WO 2006/040562 A1 | 4/2006 |
| WO | WO 2010/141695 A1 | 12/2010 |
| WO | WO 2011/057245 A2 | 5/2011 |

OTHER PUBLICATIONS

Hendricksen et al.; U.S. Appl. No. 14/659,471 entitled "Suture passer with radiused upper jaw," filed Mar. 16, 2015.

Hendricksen et al.; U.S. Appl. No. 14/697,494 entitled "Suture passers adapted for use in constrained regions," filed Apr. 27, 2015.

Asik et al.; Strength of different meniscus suturing techniques; Knee Sur, Sports Traumotol, Arthroscopy; vol. 5; No. 2; pp. 80-83; (year of publication is sufficiently earlier than the effective U.S. filed and any foreign priority date) 1997.

Asik et al.; Failure strength of repair devices versus meniscus suturing techniques; Knee Surg, Sports Traumatol, Arthrosc; vol. 10; No. 1; pp. 25-29; Jan. 2002.

Arthrex®, Arthrex, Inc., "The Next Generation in Shoulder Repair Technology," Product Brochure from Arthrex, Inc; Naples, Florida, (year of pub. sufficiently earlier than effective US filed and any foreign priority date) 2007, 22 pages.

ArthroCare® Sportsmedicine, Sunnyvale, CA, SmartStitch® Suture Passing System with the PerfectPasserTM, Product brochure, (year of pub. sufficiently earlier than effective US filed and any foreign priority date) 2006, 4 pages.

BiPass(TM) Suture Punch, Biomet® Sports Medicine, Inc., accessed Feb. 29, 2008 at <http://www.arthrotek.com/prodpage.cfm?c=0A05&p=090706> 2 pages.

Boenisch et al.; Pull-out strength and stiffness of meniscal repair using absorbable arrows or Ti-Cron vertical and horizontal loop sutures; Amer. J. of Sports Med.; vol. 27; No. 5 pp. 626-631; Sep.-Oct. 1999.

Cayenne Medical; CrossFix® II System (product webpage); 4 pgs.; downloaded Nov. 21, 2011 (www.cayennemedical.com/products/crossfix/).

Covidien Surgical; Endo Stitch 10 mm Suturing Device; accessed Dec. 4, 2012 at <http://www.autosuture.com/autosuture/pagebuilder.aspx?topicID=7407&breadcrumbs=0:63659,30691:0,309:0> 2pages.

Depuy Mitek, Inc; Raynham, MA, "Versalok Surgical Technique for Rotator Cuff Repair: The next generation in rotator cuff repair," Product brochure, (year of pub. sufficiently earlier than effective US filed and any foreign priority date) 2007, 18 pages.

Duerig, T. et al., "An overview of nitinol medical applications" Materials Science and Engineering A273-275, pp. 149-160; May 1999.

Linvatec Conmed Company, Largo, Florida, Product descriptions B17-19, B21; Tissue Repair Systems, Tissue Repair Accessories, and Master Arthroscopy Shoulder Instrument Set, (printed on or before Aug. 2007), 4 pages.

Ma et al; "Biomechanical Evaluation of Arthroscopic Rotator Cuff Stitches," J Bone Joint Surg Am, Jun. 2004; vol. 86(6):1211-1216.

Medsfera; Suturing devices; accessed Dec. 4, 2012 at <http://www.medsfera.ru/shiv.html> 13 pages.

Nho et al; "Biomechanical fixation in Arthroscopic Rotator Cuff Repair," Arthroscopy: J of Arthroscop and Related Surg; vol. 23. No. 1, Jan. 2007: pp. 94-102.

Nord et al.; Posterior lateral meniscal root tears and meniscal repair; Orthopedics Today; 5 pgs; Nov. 2010; retrieved from the internet on Aug. 21, 2014 (http://www.healio.com/orthopedics/arthroscopy/news/print/orthopedics-today/%7B1b52a700-e986-4524-ac7d-6043c9799e15%7D/posterior-lateral-meniscal-root-tears-and-meniscal-repair).

Rimmer et al.; Failure Strength of Different Meniscal Suturing Techniques; Arthroscopy: The Journal of Arthroscopic and Related Surgery; vol. 11; No. 2; pp. 146-150; Apr. 1995.

(56) References Cited

OTHER PUBLICATIONS

Schneeberger, et al; "Mechanical Strength of Arthroscopic Rotator Cuff Repair Techniques: An in Vitro Study," J Bone Joint Surg Am., Dec. 2002; 84:2152-2160.
Smith&Nephew; Fast-Fix Meniscal Repair System (product webpage); 4 pgs.; downloaded Nov. 21, 2011 (http://endo.smith-nephew.com/fr/node.asp?NodeId=3562).
Strobel; Manual of Arthroscopic Surgery (1st Edition); Springer Verlag, Hiedelberg ©2002; pp. 127-129; Dec. 15, 2001.
USS SportsMedicine ArthoSew™ Single Use Automated Suturing Device with 8.6 mm ArthroPort Cannula Set, Instructions for Use, <http:www.uss-sportsmed.com/imageServer.aspx? contentID=5020 &contenttype=application/pdf> accessed Apr. 25, 2007, 2 pages.
USS SportsMedicine ArthroSew™ Suturing Device, <http://www.uss-sportsmed.com/SportsMedicine/pageBuilder.aspx? webPageID=0&topicID=7141&xsl=xsl/productPagePrint.xsl>, product description, accessed Apr. 25, 2007, 3 pages.
Dictionary.com; Adjacent (definition); 5 pgs.; retrieved from the internet (http://www.dictionary.com/browse/adjacent) on Apr. 5, 2016.
Murillo et al.; U.S. Appl. No. 15/012,790 entitled "Suture passer devices and methods," filed Feb. 1, 2016.
Hendricksen et al.; U.S. Appl. No. 15/054,072 entitled "Suture passer with radiused upper jaw," filed Feb. 25, 2016.
Hirotsuka et al.; U.S. Appl. No. 15/132,211 entitled "Pre-tied surgical knots for use with suture passers," filed Apr. 18, 2016.
George et al.; U.S. Appl. No. 15/145,627 entitled "Arthroscopic knot pusher and suture cutter," filed May 3, 2016.
Murillo et al.; U.S. Appl. No. 15/216,482 entitled "Automatically reloading suture passer devices that prevent entanglement," filed Jul. 21, 2016.
Peter et al.; U.S. Appl. No. 15/283,749 entitled "Knot tying accessory," filed Oct. 3, 2016.
Murillo et al.; U.S. Appl. No. 15/289,054 entitled "Automatically reloading suture passer devices and methods," filed Oct. 7, 2016.
Saliman; U.S. Appl. No. 15/853,531 entitled "Suture methods for forming locking loops stitches," filed Dec. 22, 2017.
Saliman et al.; U.S. Appl. No. 15/866,343 entitled "Meniscus repair," filed Jan. 9, 2018.
Saliman et al.; U.S. Appl. No. 15/918,969 entitled "Transosteal anchoring methods for tissue repair," filed Mar. 12, 2018.
Ceterix; Novocut suture manager; retrieved from the internet (https://web.archive.org/web/20150314071511/http://www.ceterix.com:80/im-a-physician/products/) on Oct. 11, 2017; 1 page; Mar. 12, 2015.
Ceterix; Novocut suture manager; retrieved from the internet (https://www.youtube.com/watch?v=6txqBJxvnuA) on Oct. 11, 2017; 1 page; Mar. 5, 2015.
Chinese Notification to Grant Patent Right for Invention Application No. 201510163638.1 dated May 28, 2019.
Chinese Notification of Correction of Notice of Grant of Patent Right for Invention Application No. 201510163638.1 dated Jun. 5, 2019.

\* cited by examiner

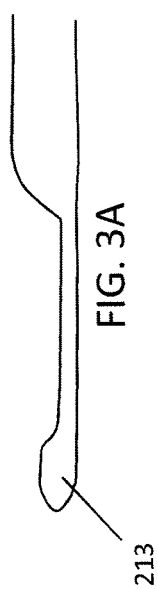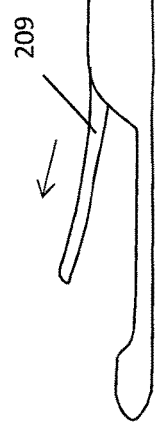
FIG. 3A  FIG. 3B  FIG. 3C  FIG. 3D  FIG. 3E
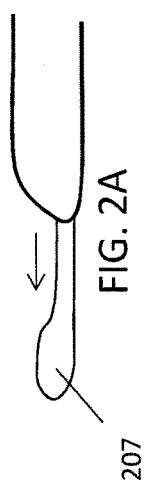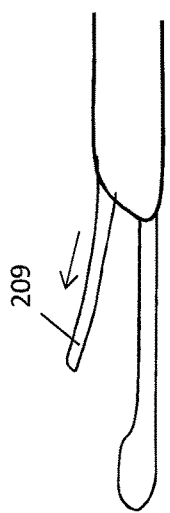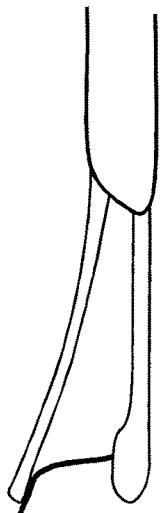
FIG. 2A  FIG. 2B  FIG. 2C  FIG. 2D  FIG. 2E

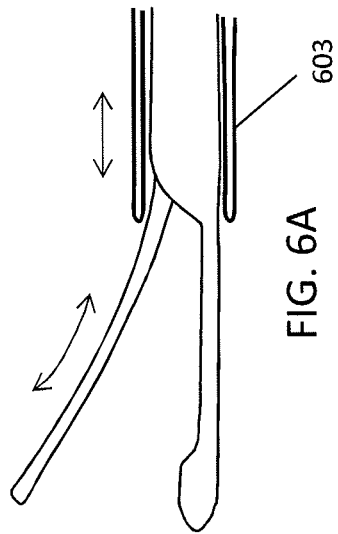
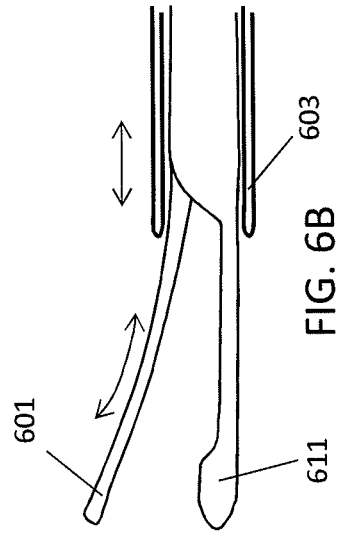
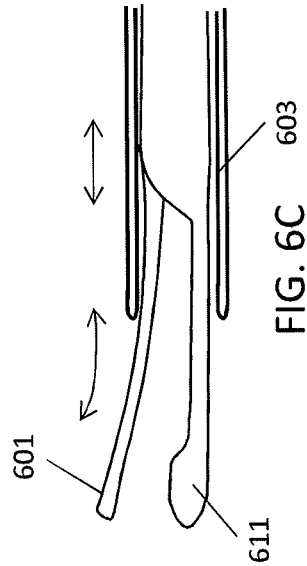
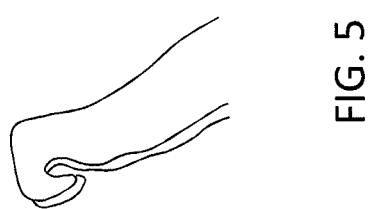
FIG. 5

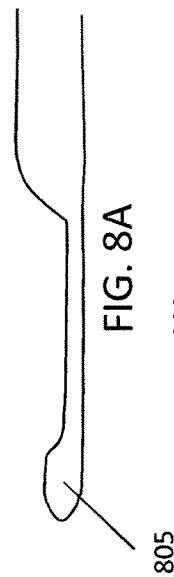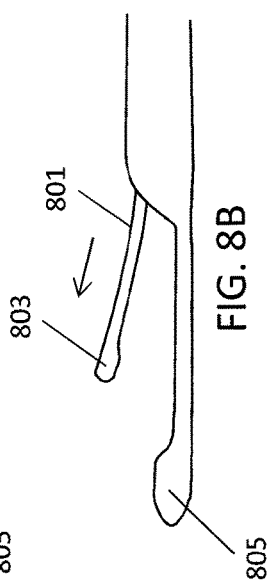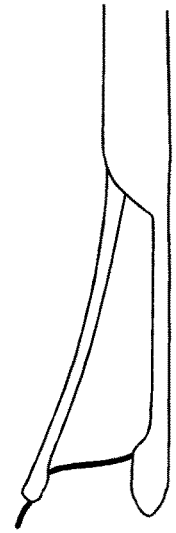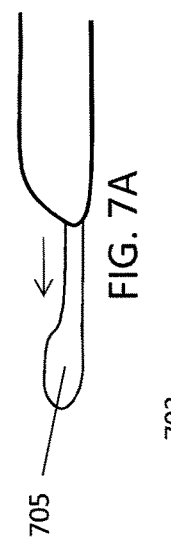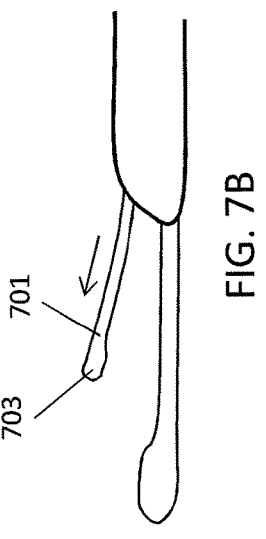

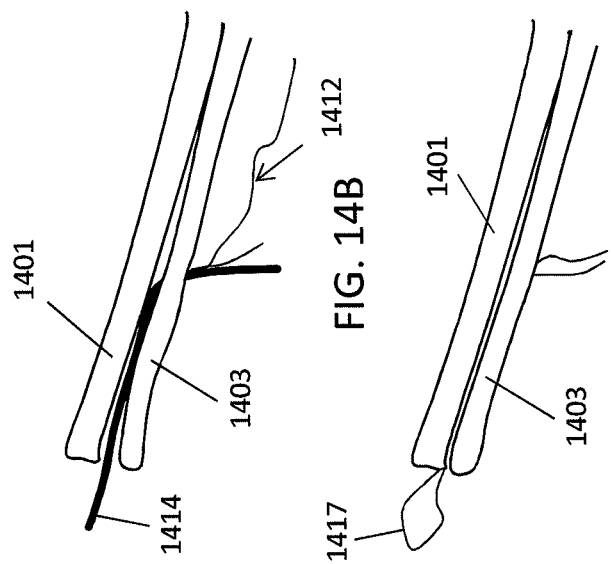
FIG. 14B
FIG. 14C
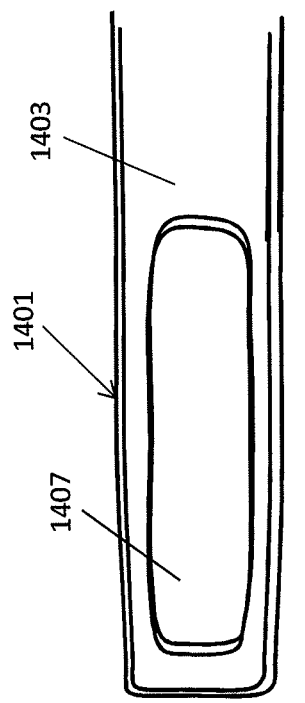
FIG. 14A

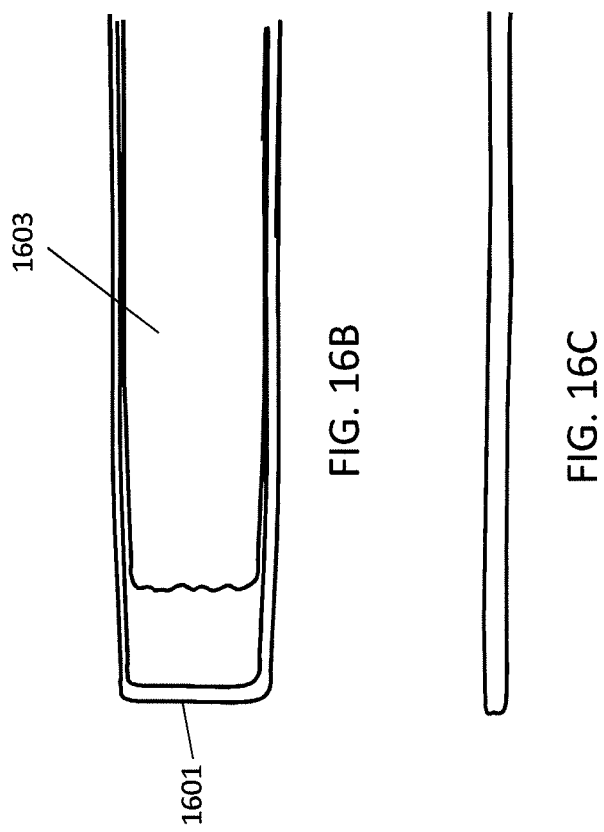

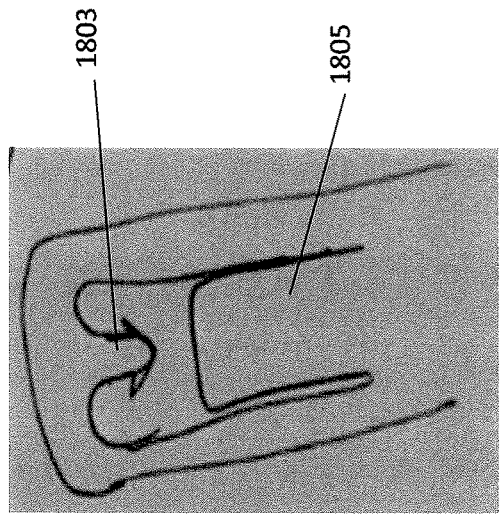
FIG. 18
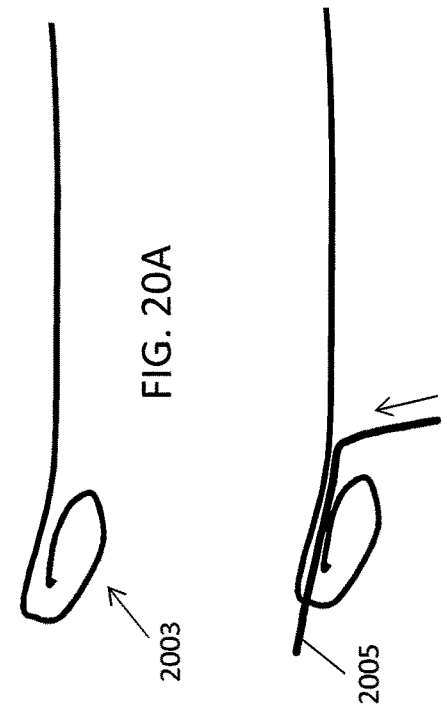
FIG. 20A
FIG. 20B
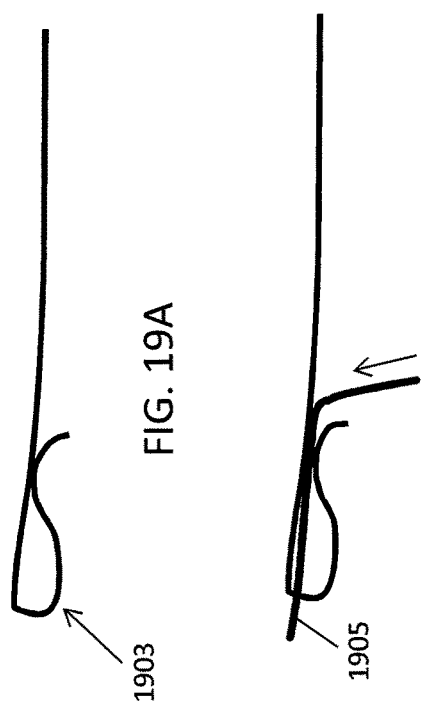
FIG. 19A
FIG. 19B

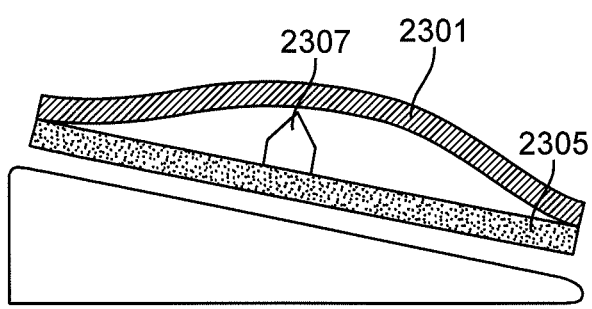
FIG. 23
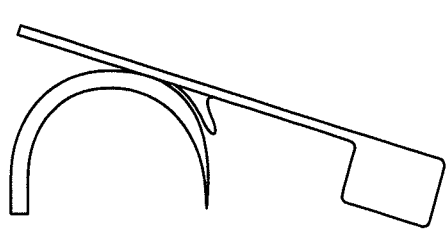 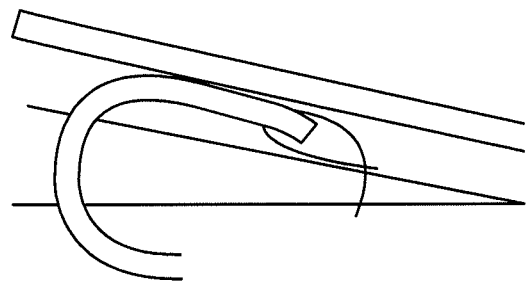
FIG. 24A		FIG. 24B

SUTURE PASSERS ADAPTED FOR USE IN CONSTRAINED REGIONS

CROSS REFERENCE TO RELATED APPLICATION

This application claims the benefit of U.S. Provisional Patent Application No. 61/976,742, filed Apr. 8, 2014, titled "SUTURE PASSERS ADAPTED FOR USE IN CONSTRAINED REGIONS". This application is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Suture passer apparatus, including devices and systems, as well as methods of making and using such apparatus are described herein. In particular, suture passer apparatus adapted for use in narrow, confined, and/or difficult to access regions of a body, such as a knee joint.

BACKGROUND

Suturing of tissue during surgical procedures is time consuming and can be particularly challenging in difficult to access body regions and regions that have limited clearance, such as regions partially surrounded or covered by bone. For many surgical procedures, it is necessary to make a large opening in the human body to expose the area requiring surgical repair. However, in many cases, accessing the tissue in this manner is undesirable, increasing recovery time, and exposing the patient to greater risk of infection.

Suturing instruments ("suture passers" or "suturing devices") have been developed to assist in accessing and treating internal body regions, and to generally assist a physician in repairing tissue. Although many such devices are available for endoscopic and/or percutaneous use, these devices suffer from a variety of problems, including limited ability to navigate and be operated within the tight confines of the body, risk of injury to adjacent structures, problems controlling the position and/or condition of the tissue before, during, and after passing the suture, and difficulties loading the suture into the device, particularly for threading multiple suture loops.

For example, some surgical instruments used in endoscopic procedures are limited by the manner in which they access the areas of the human body in need of repair. In particular, the instruments may not be able to access tissue or organs located deep within the body or that are in some way obstructed. In addition, many of the instruments are limited by the way they grasp tissue, apply a suture, or recapture the needle and suture. Furthermore, many of the instruments are complicated and expensive to use due to the numerous parts and/or subassemblies required to make them function properly. Suturing remains a delicate and time-consuming aspect of most surgeries, including those performed endoscopically.

Some variations of suture passers, such as those described in U.S. Pat. No. 7,377,926 to Taylor, have opposing jaws that open and close over tissue. One, or in some variations, both, jaws open, scissor-like, so that tissue may be inserted between the open jaws. Unfortunately, such devices cannot be adequately positioned for use in hard to navigate body regions such as the joints of the body, including the knee (e.g., meniscus) and the shoulder because there is not room within the confines of the body (e.g., joint region) to open the scissoring jaws.

The knee joint is one example of a tissue region that is notoriously difficult to access. For example, the meniscus is a C-shaped piece of fibrocartilage which is located at the peripheral aspect of the joint (e.g., the knee) between the condyles of the femur and the tibia on the lateral and medial sides of the knee. The central two-thirds of the meniscus has a limited blood supply while the peripheral one third typically has an excellent blood supply. Acute traumatic events commonly cause meniscus tears in younger patients while degenerative tears are more common in older patients as the menisci become increasingly brittle with age. Typically, when the meniscus is damaged, a torn piece of meniscus may move in an abnormal fashion inside the joint, which may lead to pain and loss of function of the joint. Early arthritis can also occur due to these tears as abnormal mechanical movement of torn meniscal tissue and the loss of the shock absorbing properties of the meniscus lead to destruction of the surrounding articular cartilage. Occasionally, it is possible to repair a torn meniscus. While this may be done arthroscopically, surgical repair using a suture has proven difficult to perform because of the hard-to-reach nature of the region and the difficulty in placing sutures in a way that compresses and secures the torn surfaces.

Arthroscopy typically involves inserting a fiberoptic telescope that is about the size of a pencil into the joint through an incision that is approximately ⅛ inch long. Fluid may then be inserted into the joint to distend the joint and to allow for visualization of the structures within that joint. Then, using miniature instruments which may be as small as 1/10 of an inch, the structures are examined and the surgery is performed.

The meniscus of the knee is just one example of a tissue that is difficult to access so that appropriate suturing may be performed.

Thus, there is a need for methods and apparatuses (e.g., devices and systems) for suturing tissue, particularly tissue in difficult to access regions of the body including the joints (shoulder, knee, etc.). In particularly, it has proven useful to provide a device that may simply and reliably reach and pass sutures within otherwise inaccessible tissue regions. Such devices should be extremely low profile, and may be adapted or otherwise configured to fit in the tight spaces of the joints. Finally, would be useful to provide suturing apparatuses that allow selective and specific penetration of the tissue by both the tissue penetrator (needle element) and a jaw so that complex (including right-angled) suturing patterns may be achieved.

There is also a need for methods and apparatuses for suturing tissue. In particular, it has proven useful to provide a device that may simply and reliably reach and pass sutures within otherwise inaccessible tissue regions. Further, there is a need for suture passers that can be automatically loaded (or preloaded) pass multiple lengths (e.g., bights) of suture though the tissue without requiring that they be manually reloaded, either within the tissue or by withdrawing them from the tissue.

Although limited space in tight joints is frequently a limiting factor in soft tissue repair within joints, described herein are apparatus configured to facilitate suture passing in such tight joints. The apparatus (e.g., devices and systems)

described herein may pass sutures vertically through soft tissue, with a tissue penetrator (e.g., needle) that extends out of a lower jaw at or near a 90° angle. After passing through the tissue, the tissue penetrator contacts an upper jaw (or in come variations, a condyle protective element), which deflects the needle again, so that the needle extends in a serpentine path, either deflected distally or deflected proximally.

SUMMARY OF THE DISCLOSURE

In general, described herein suture passer apparatus (devices and systems) that may be used to suture tissue within a narrow, confined space.

For example, a suture passer may include an elongate body and a fixed or laterally movable (e.g., extendable and retractable) lower jaw member from which a tissue penetrator (needle) may extend. The tissue penetrator may be held within the lower jaw member and may be extended distally from a side region of the lower jaw member and deflected from the side of the lower jaw through the tissue, particularly when the tissue is held between the lower jaw and an upper jaw. The lower jaw may be bent or straight. In some variations the lower jaw may be hinged or bendable. The suture passer may also include an upper jaw that acts as a shield or deflector to deflect the needle (tissue penetrator) after it extends through the tissue from the lower jaw. The upper jaw may be adapted to extend from within the elongate body. The upper jaw may be extremely thin and sufficiently strong to deflect the tissue penetrator. In some variations the upper jaw is pre-biased to curve away from the elongate axis of the elongate body, e.g., to form a v-shaped opening when extended.

The upper jaw may include a suture securing region near its distal end so that a suture passed by a tissue penetrator is held by the upper jaw until the device is retracted from the tissue.

Some variations of suture passers and methods described herein include only a lower jaw that is fixed or bendable and/or slidable. The lower jaw houses a tissue penetrator that may be extended laterally from a side-opening in the lower jaw. Although an upper jaw is not included, a separate shield member may be positioned laterally from the target tissue to be sutures, and used to deflect the tissue penetrator from non-target tissue.

In variations including an upper arm (opposite from the arm housing the tissue penetrator) may also include a suture retainer on upper arm. For example, the upper arm may include a passage, opening, or loop through which the tissue penetrator passes after being deflected against a tissue deflection surface. When the tissue penetrator is retracted back through the tissue, the suture (which may be loaded into the tissue penetrator and pushed through the tissue from the lower jaw with the tissue penetrator) may be retained. A loop or bight of tissue may be passed and retained on the opposite side of the target tissue, e.g., in the upper arm. In some variations the second (upper) jaw may include a suture retainer that includes a leaf spring or other clamping mechanism that clamps the suture between two or more surfaces to hold it. In some variations the upper jaw includes a region that is adapted to be penetrated by the tissue penetrator (e.g., a mesh region, a region that is made of a "soft" material such as silicone, etc.); when retracting the needle back to the lower jaw, the suture will be retained by the upper jaw.

Also described herein are suture passer apparatus having lower jaws (housing the tissue penetrator) that have very narrow (e.g., less than 20 mm, less than 10 mm, less than 5 mm) widths. When operating these devices, they may be turned sideways to position within a confined space, and rotated over to operate. The distal end of the suture passer, and in particular a suture passer having a very narrow lower jaw, may be bent or curved to one side, enhancing positioning within the narrow confines of the tissue.

BRIEF DESCRIPTION OF THE DRAWINGS

In FIG. 1B, a side view of the distal end region of the suture passer includes a lower jaw that houses a tissue penetrator and is configured to slide distally to proximally relative to (e.g., from) the distal end of the elongate body. An upper jaw comprising a pre-bent or curved strip of metal is adapted to deflect the tissue penetrator distally (though it may be adapted to deflect it proximally).

FIG. 1C is similar to FIG. 1B, except the lower jaw member is fixed relative to the elongate body and does not slide distally to proximally. As in FIG. 1B, the upper jaw may slide/extend distally and retract proximally from the elongate body and deflect the tissue penetrator.

FIG. 1D is similar to FIG. 1B, however the upper jaw is adapted to include a passage or deflector and/or tissue retainer at the distal end that retains the bight of suture after is passed from the lower jaw to the upper jaw.

FIG. 1E is similar to FIG. 1D except the lower jaw (as in FIG. 1C) is fixed relative to the elongate body.

FIGS. 2A-2E illustrates operation of a suture passer having a distal end with a sliding lower jaw housing a tissue penetrator and an upper jaw adapted as a thin deflector that extends and retracts into the elongate body (including, in some variations, completely retracting into the elongate body). In FIG. 2A, the lower jaw with the tissue penetrator (which may be pre-loaded with suture) is extended and may be positioned against a target tissue. In FIG. 2B the upper jaw extends from the elongate body so that a target tissue (such as a meniscus of the knee) is positioned between the upper and lower jaws. In FIG. 2C the upper and lower jaws are completely extended. In FIG. 2D the tissue penetrator (needle) is extended laterally from within the lower jaw and extended across the tissue between the jaws. In FIG. 2E the tissue penetrator is deflected a second time so that it is directed distally by the upper jaw. The tissue penetrator may carry a suture bight through the tissue and it may be retained on the opposite side of the tissue, either by a suture retainer region or by friction between the tissue and suture, or both.

FIGS. 3A-3E illustrates a similar method of operating a suture passer having a fixed lower jaw (e.g., fixed and non-slideable relative to the elongate body).

FIG. 5 illustrates one variation of an upper jaw having a hook at the distal end. The hook may be used to capture and pull a bight of suture that has been passed through the tissue.

FIGS. 6A-6C illustrate the operation of a suture passer having a clamping collar, configured as an outer collar or tube that can be used to close the 'jaws' formed by an upper and lower jaw member of any of the distal end variations described, including those shown in FIGS. 1B-1E. This may allow the device to clamp on the target tissue held between the jaws, as illustrated.

FIGS. 7A-7E illustrate operation of a variation of the distal end of a suture passer device such as the one shown in FIG. 1D, in which the lower jaw is axially slideable distally to proximally, as is the upper jaw, and the upper jaw include a suture retainer region at the distal end. In general, the upper and lower jaws are independently movable (and slideable) as is the tissue penetrator.

FIGS. 8A-8E illustrates a side view of the operation of a variation of the distal end of a suture passer device such as the one shown in FIG. 1E, in which the lower jaw is fixed relative to the elongate body and the upper jaw is axially slideable distally to proximally, and the upper jaw include a suture retainer region at the distal end.

In FIG. 11 the suture material is a woven material that includes a shape set material that helps hold the bight of suture open.

FIG. 14A shows a bottom view of one variation of an upper jaw (second jaw) having an opening into which the tissue penetrator may extend; the upper jaw is formed of a pair of leaflets with one leaflet being deflectable from the other so that the tissue penetrator can extend through the hole/opening and between the leaflets and distally out of the upper jaw, as illustrated in the side views of FIGS. 14B and 14C. Retracting the tissue penetrator leaves a loop or bight of suture behind, as shown in FIG. 14C.

FIGS. 16B and 16C show bottom and side views, respectively.

FIG. 18 illustrates another distal end of a suture passer apparatus having a suture retainer region at the upper jaw as well as a deflection region that may be displaced relative to the rest of the upper jaw when the tissue penetrator extend from the lower jaw.

FIGS. 19A and 19B illustrate another variation of an upper jaw including a suture retainer region.

FIGS. 20A and 20B show another variation of an upper jaw including a suture retainer region.

FIG. 23 shows another variation of an upper jaw including a suture retainer region configured as a soft material attached to a more rigid or hard material that is adapted to retain a bight of suture passed from the opposite jaw by the tissue penetrator.

FIGS. 24A and 24B illustrate another variation of a tissue penetrator having an upper jaw that is adapted to deflect a tissue penetrator and retain a bight of suture passed by the tissue penetrator to the upper jaw.

DETAILED DESCRIPTION

In general, described herein are suture passer apparatus and methods of making and using them. Any of the suture passer apparatuses described herein may include features or elements that may be adapted for use with any of the other features or elements of the suture passers, except where specifically noted.

For example, described herein are suture passers that are particularly well adapted for insertion and manipulation in tight, narrow and difficult to access regions. Suture passers previously described, and illustrated in FIGS. 36A-36B, included an elongate body 3601 with a proximal handle region having controls for operating the apparatus. The distal end included a lower jaw member 3605 that is axially (distally-to-proximally) slideable relative to the elongate body, and an upper jaw member 3603 that is bent or bendable relative to the elongate body and/or the lower jaw. For example, the upper jaw may be pivotably attached 3613 to the end region of the elongate body 3601 so that it could be bent and clamp onto tissue held between the upper and lower jaws when the lower jaw was axially (distally) extended. A needle (also referred to generically as a tissue penetrator) which can carry a suture or loop (bight) of suture housed with the lower jaw may be extended laterally from a side of the lower jaw so that the tip of the tissue penetrator extends across the jaw formed by the upper and lower jaws and contacts the upper jaw where it is deflected distally or proximally. The suture may be retained by the upper jaw (or in the tissue near the upper jaw) when the tissue penetrator is retracted.

Thus, described herein are variations of suture passers that include a laterally (axially) retractable upper jaw that may be extremely thin (e.g., less than 10 mm, less than 5 mm, less than 4 mm, less than 3 mm, less than 2 mm).

Figure 1A:
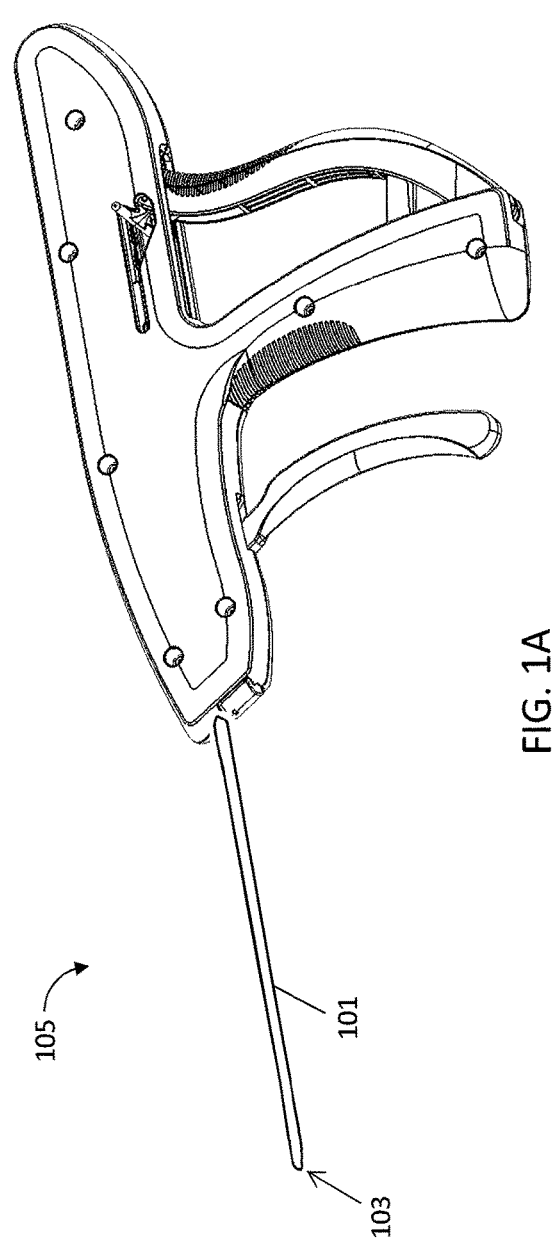
FIG. 1A shows an example of a suture passer device having an elongate body with a proximal handle region and a distal lower jaw housing a tissue penetrator that can exit from a lateral opening to extend perpendicularly (or nearly perpendicularly) from the lower jaw.
Figure 1C:
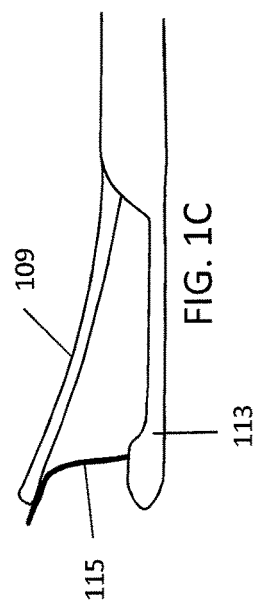
FIGS. 1B-1E show variations of different distal jaw regions that may be used with the elongate body and handle regions shown in FIG. 1A.

FIG. 1A shows a body of an elongate suture passer including an elongate body extending distally from a proximal handle 105. The elongate body 101 has a distal end 103 to which a first (and in some variations a second) jaw may extend and/or be attached. The proximal handle 105 may include controls for controlling the movements of the jaw(s), and tissue penetrator. FIGS. 1B-1E illustrate various distal end configurations. For example, in FIG. 1B, the distal end includes a lower jaw member 107 that is configured to slide axially distally and proximally relative to the elongate body (e.g., in line with the elongate body). The upper jaw 109 is also configured to slide distally and proximally from within the elongate body to form a distal-facing (v-shaped) opening surrounding the tissue to be sutured. In FIG. 1B, the upper jaw is thin and acts as a protective member that prevents the tissue penetrator 115 (shown extended in FIG. 1B) from extending across the jaws and into the opposite side; instead, the tissue penetrator 115 is deflected distally along the bottom of the upper jaw member 109.

The upper jaw in the variation shown in FIG. 1B is similar to that shown in FIG. 1B, however the lower jaw member 113 does not move axially, but is instead fixed, and may be integral with, the elongate body. The lower jaw 107 in FIG. 1D is similar to the lower jaw of FIG. 1B, however, the upper jaw 111 includes a suture capture region 119 (which may also be referred to as a suture retainer, trap, suture capture, or suture snare) at or near the distal end region. The tissue penetrator 115 extending from the lower jaw member passes through the upper jaw 111 so that it extends out of the distal end of the upper jaw; when the tissue penetrator is retracted back into the lower jaw 107, a suture being pushed through the tissue by the tissue penetrator from the lower jaw member will remain held by the suture retainer 119 in the upper jaw 111. Any appropriate suture retainer may be used. Examples of suture retainer regions are described below, and may include a leaf-spring region that is displaced by the tissue penetrator as well as edge (e.g., jagged) regions that may trap and/or hold the suture.

Figure 1E:
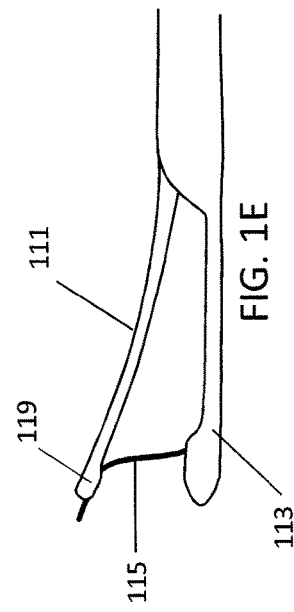
Figure 1B:
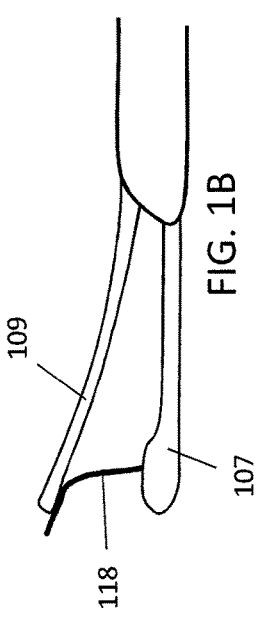
Figure 1D:
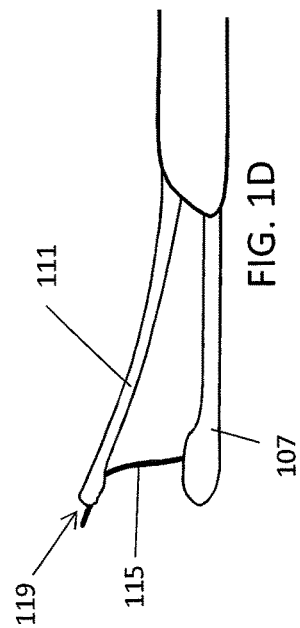

FIG. 1E also shows a side perspective view of a distal end of a suture passer as described above, having a lower jaw member that is fixed and extends from the distal end of the elongate body, and an upper jaw member that is axially slidable and include a suture retainer region 119.

The variations shown in FIGS. 1B-1E are suture passers with very thin upper jaws (e.g., the upper jaw may be less than 2 mm thick, less than 1 mm thick, less than 0.5 mm thick, etc.). When used in knee meniscus repair, the primary purpose of this upper jaw is to protect condyle surfaces from the needle that comes out of the lower jaw. Protection of the condyle is achieved by having the thin upper jaw be hard enough to deflect the needle. The upper jaw may be sufficiently bendable to curve and bend away from the lower jaw as it is extended out of the elongate body, as illustrated. For example, the upper jaw may be formed of a shape memory material such as Nitinol.

FIGS. 2A-2E illustrate the distal end variation shown in FIG. 1B in operation. To position the tissue penetrator around a target tissue, the lower jaw member 207 may be first extended distally from the distal end of the elongate body, as shown in FIG. 2A. Thereafter, or before the lower jaw has been completely extended, the upper jaw 209 may be extended from the distal end of the elongate body, as shown in FIG. 2B. In FIG. 2C, both the upper and lower jaws have been fully extended around a target tissue (e.g., the meniscus in a knee). Thereafter, as shown in FIG. 2D, the tip of the tissue penetrator 215 housed completely within the lower jaw may be extended from the lower jaw, though the tissue and against the upper jaw, where the tip is deflected distally. A suture, e.g., a loop or bight of suture, may be include and may be passed with the tissue penetrator from the lower to the upper jaw.

FIGS. 3A-3E illustrate the operation of a distal end of suture passer similar to the variation shown in FIG. 1C, having a rigidly fixed lower jaw 213. The extended lower jaw 213 may be positioned within the tissue, e.g., on one side of the target tissue, and typically has a narrow and thin profile, allowing it to be positioned within the tissue and into even difficult to access regions. As described below in reference to FIGS. 9A and 9b, the lower jaw may be bent (or in other variations, bendable). In FIG. 3A-3E the lower jaw does not slide distally or proximally relative to the elongate body; instead, only the upper jaw 209 slides distally and proximally. In FIG. 3B, the upper jaw 209 is shown extended distally. FIG. 3C shows the upper jaw fully extended and the tissue penetrator is then extended across the tissue as shown in FIG. 3D-3E.

Figure 4A:
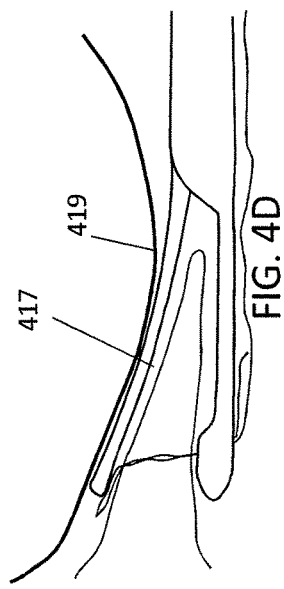
FIGS. 4A-4F illustrate operation of a suture passer passing a pair of suture bights using a suture passer having a distal end similar to the one shown in FIGS. 1C and 3A-3E. The distal end of the suture passer is shown in profile, while the tissue is shown transparent (e.g., in partial section) to illustrate the passage of the needle and suture therethrough.
Figure 4B:
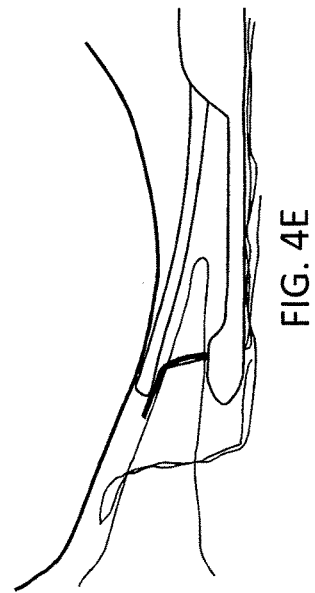
Figure 4C:
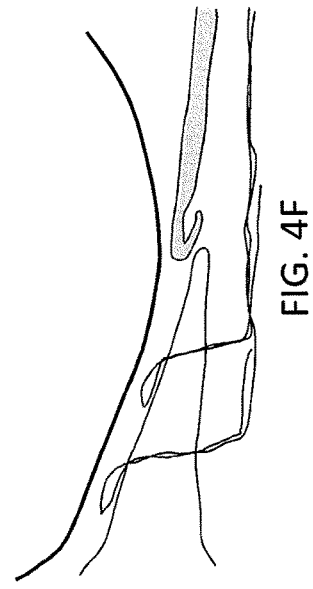
Figure 4D:
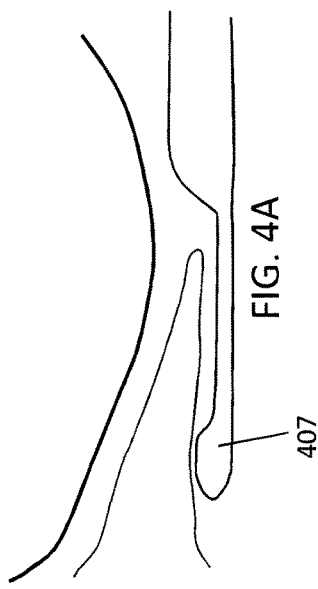
Figure 4E:
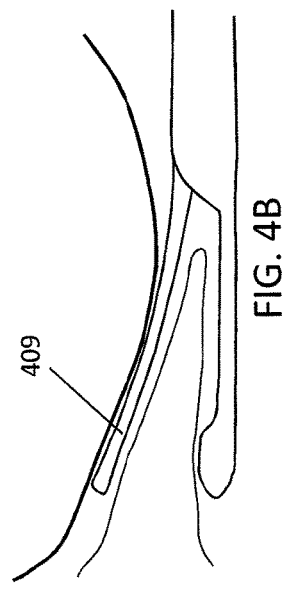
Figure 4F:
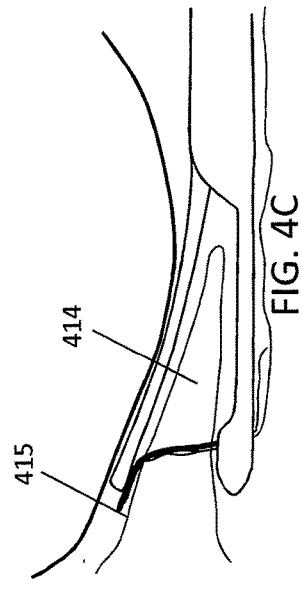

FIGS. 4A-4F illustrate the operation of one variation of a tissue penetrator as described above. The distal end of the tissue penetrator illustrated in FIGS. 4A-4F has a fixed lower jaw 407 that is rigidly connected to the distal end region of the elongate body, and a thin, strong, upper jaw deflector 409 can be extended distally by sliding out of the elongate body and curving up slightly as it extends outward. In FIG. 4A, the lower jaw member may be positioned on one side of the meniscus, and the upper jaw member may be extended from the distal end of the elongate body (the proximal end of the lower jaw member), as shown in FIG. 4B. In FIG. 4C, the tissue penetrator 415 is extended across and though the meniscus 414 between the upper and lower jaws, passing a loop (bight) of suture though the meniscus along with the tissue penetrator. The tissue penetrator (needle) and suture are passed through the meniscus. The tissue penetrator deflects off the upper jaw away from the femoral condyle and carries a bight of suture beyond the superior surface of the meniscus. In FIG. 4D the tissue penetrator has been retracted, leaving the first bight of suture through the meniscus and between the superior surface of the meniscus 417 and the femoral condyle 419. The tissue penetrator is retracted, leaving behind the suture bight (the friction between the needle hole through the meniscus and the suture retains the suture as the needle is retracted). The suture passer may then be repositioned around the tissue, loaded with the second bight of suture (which may be, for example, the opposite end of the suture forming the first loop) and against passed through the tissue, as shown in FIG. 4E. The suture passer has been moved to a new location, and another bight of suture is passed through the meniscus in the same manner as shown in FIGS. 4C and 4D. Once the suture passer is removed, the two bight regions extending through the meniscus may be grasped and pulled and/or knotted (e.g., to each other) to secure the tissue, as shown in FIG. 4F. For example, the suture passer may be pulled away from the suture bights, leaving the suture bights in location through the meniscus. A second tool is then used to retrieve the suture bights. Such a tool could be a hook, a crab claw, etc. In some variations a hook or grasper may be used, including an upper jaw having a hook region allowing it to grip and manipulate the suture loops, as illustrated in FIG. 5. In FIG. 5, a hook feature exists at the end of the upper jaw, allowing the suture passer upper jaw to be the tool used to retrieve the suture bights.

The method shown in FIGS. 4A-4F illustrates operation of a device having an upper jaw without a suture trap (suture capture region). In some variations, the lower jaw may also be fixed (e.g., does not slide axially relative to the elongate shaft/body) to facilitate a device shaft that is as thin as possible by eliminating internal features that allow for a sliding lower jaw.

In any of the variations described herein, the upper and lower jaws of the suture passer may be adapted to clamp, gab, grasp or otherwise hold secure the tissue between the upper and lower jaw to prevent it from tearing during the procedure, and from moving when the tissue penetrator is applied against the tissue. This may reduce misalignment of needle as it is passed through the tissue.

Thus, any of the devices described herein may be adapted to include a clamping element, such as a sleeve, tube, etc., that drives or allows the distance (e.g., angle) between the upper and lower jaws to be reduced. For example, in FIGS. 6A-6C, an outer cannula 603 (e.g., sleeve) may be driven distally to push against the outer sleeve, causing the thin, and somewhat flexible upper jaw member 601 to close towards the lower jaw 611, as shown in the progression from FIGS. 6A-6C. Similarly, moving the sleeve/cannula proximally allows the upper jaw to expand up and away from the lower jaw, further opening the distal-facing opening.

In FIGS. 6A-6C, the thin upper jaw is shown as an upper jaw that can be advanced and retracted from the device shaft, perhaps telescopically, while the lower jaw is fixed relative to the distal end of the elongate body. Having the upper jaw retracted allows the device to be easily inserted into the joint, and in the case of the knee, may allow the lower jaw to be easily inserted underneath the meniscus. Then, due to its thinness, the upper jaw can readily be advanced above the meniscus. The clamping mechanism (cannula or sleeve) that is shown in FIGS. 6A-6C as a tube. As mentioned, by advancing the clamping mechanism, the upper jaw clamps down on the lower jaw, compressing any tissue between the upper and lower jaws. Retracting the tube allows the clamp to be released.

FIGS. 7A-7E illustrate the operation of the suture passer device having a sliding upper and sliding lower jaw that may both be independently slide (axially) into and out of the distal end region of the elongate body to form a v-shaped distal opening, as described above for FIG. 1D. In this example, the upper jaw 701 is thin, but includes a suture retainer region 703 at the distal end portion of the upper jaw. To position the device, the lower jaw 705 may be extended from the distal end of the elongate body and slide under or adjacent to a target tissue. The upper jaw may then be extended out of the distal end of the elongate body and extend across the target tissue from another side. Once the tissue is held between the jaws, as shown in FIG. 7C, a needle (tissue penetrator) may be extended from the lower jaw toward the upper jaw, as shown in FIG. 7D. The needle may be a bendable, yet sharp, member having a sufficient column strength to be pushed through tissue while carrying a suture (e.g., in a hook, eye, or other portion at or near the distal end of the tissue penetrator). For example, a tissue penetrator may be a stainless steel or Nitionol material that is extended distally in the lower jaw until it is deflected at the lateral opening in the lower jaw to direct the tip of the tissue penetrator out of the lower jaw laterally at nearly 90° relative to the long axis of the lower jaw. In the example shown in FIG. 7E, the tip of the tissue penetrator eventually contacts the upper jaw 701, where it is deflected by the upper jaw and directed distally (although as mentioned, it could be directed proximally). The tissue penetrator in FIG. 7E passes through a channel, or opening that is configured as a suture retainer/trap 703. The suture retainer catches and holds the suture (e.g., suture loop/bight) when the tip of the tissue penetrator is retracted back to the lower jaw (not shown).

FIGS. 8A-8E illustrate a similar mechanism of operation for a suture passer such as the suture passer distal end region shown in FIG. 1E. In FIGS. 8A-8E, as in FIGS. 7A-7E, the upper jaw 801 includes a suture retainer/trap 803, however in FIGS. 8A-8E the lower jaw 805 is fixed (e.g., does not slide) relative to the upper jaw.

Figure 9A:
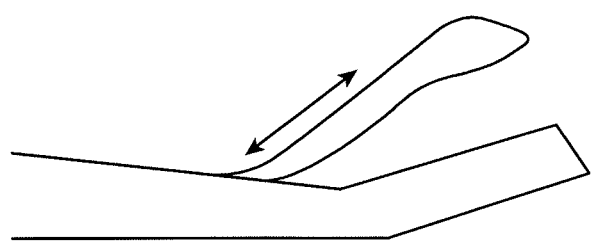
FIGS. 9A and 9B show a variation of a suture passer having a bent or curved lower jaw (in this example the lower jaw is fixed relative to the elongate body), and an axially sliding upper jaw that is adapted to deflect the tissue penetrator from the lower jaw).
Figure 9B:
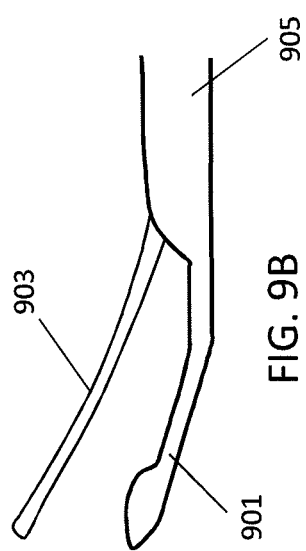

Any of the suture passers described herein may include a bend or bendable region in an upper or lower jaw to help position the distal end of the device in even narrow and constrained regions of a tissue such as a knee or shoulder joint. For example, FIGS. 9A and 9B illustrate an apparatus having a lower jaw that is fixed relative to the more proximal elongate body from which the lower jaw 901 extends. As shown in the profile view of FIGS. 9A and 9B, the fixed lower jaw 901 is angled or curved relative to the elongate body region 905 of the apparatus. The very thin upper jaw 903 is configured as a deflector for a tissue penetrator, as mentioned above, and can be advanced and retracted into the elongate body 905. The angled or curved lower jaw is intended to provide a shape that provides easier access in tight joints.

Figure 10A:
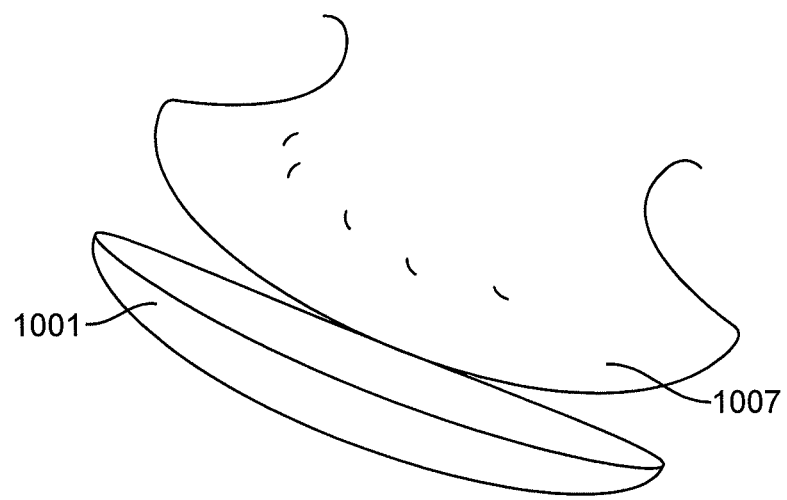
FIGS. 10A and 10B illustrate the use of a suture passer having just a lower jaw with a lateral opening from which a tissue penetrator may extend. Instead of an upper jaw that deflects and/or guides the tissue penetrator, a separate shield or deflector may be used over the tissue.
Figure 10B:
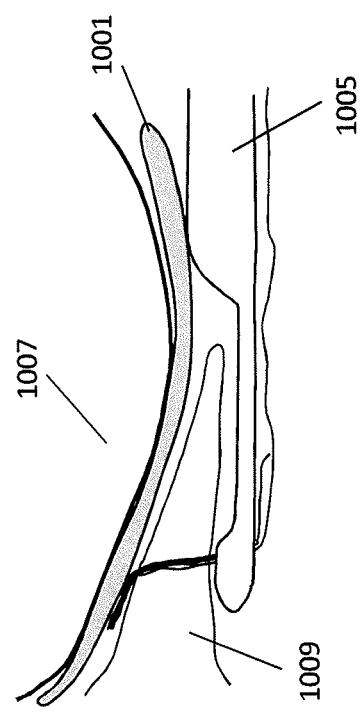

In general, the upper (or second) jaw is configured to deflect the tissue penetrator that laterally exits from the distal end region of the lower jaw at an angle (e.g., an angel between 60-125 degrees, relative to the long axis of the lower jaw and/or the long axis of the elongate body). However, in some variations an integrated upper jaw/deflector is not included, but instead a separate shield/deflector member may be used. FIGS. 10A and 10B illustrate the use of a separate shield 1001 with a "one armed" suture passer 1005. In FIGS. 10A and 10B, a knee joint including a femoral condyle 1007 is shown. The shield may be inserted before the procedure is performed, and is a protective shield 1001 that is placed between the femoral condyle 1007 and the meniscus 1009 prior to suture passing. After placing the shield, the suture passer 1005, the distal end of which consists of only a shaft and fixed lower jaw, is slid underneath the meniscus 1009. The tissue penetrator and suture are then passed from the lower jaw, through the meniscus, and then the tip of the tissue penetrator deflects off of the shield away from the femoral condyle. The simplicity of the suture passer apparatus in his example (without a second jaw member) may allow the size of the device to be minimized.

Figure 11:
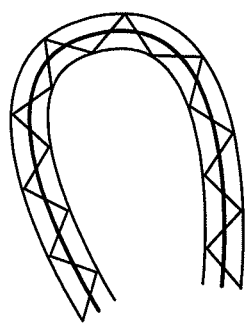
FIG. 11 illustrates one variation of a suture that may be used, in which a shape memory material (e.g., metal, plastic, etc.) or a material having a relative stiffness may be used to help form and/or hold open the loop of suture that is passed by the apparatus.

All of the methods and apparatuses described herein typically include the use of a suture. An appropriate suture may be used. For example, braided or monofilament suture, and/or sutures of any appropriate material, including bioabsorbable materials (e.g., polymeric materials). It may be of benefit to make the suture bight self-expanding or opening, to allow the suture bight to be more easily captured by a tool, or in some variations by the second/upper jaw. For example, if the apparatus does not include a suture capture region (e.g., on the second or upper jaw member), a self-expanding suture may be more easily captured if the bight is opened on the superior surface of the meniscus after suture passing; this may make it easier to retrieve with a tool. As shown in FIG. 11, the suture forming the suture bight may include a shape set material (e.g., Nitinol wire) within or on the suture. For example, the suture may include an over-braid having a shape-set wire within the braid. When the bight exits the meniscus after suture passing, the wire expands to create a large open loop that provides an easy target for a retrieval tool.

Figure 12A:
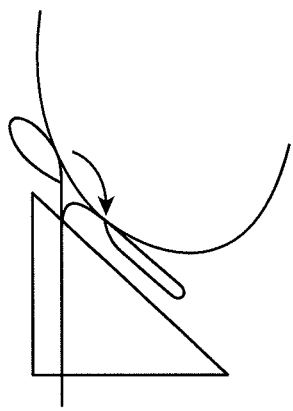
FIG. 12A shows flipping of a bight of suture that has been passed through a target tissue (shown as a meniscus) so that the suture bights are changed from a proximal orientation (as pushed by a suture passer that extends distally) to be oriented distally, which may allow them to be more easily grasped and manipulated.
Figure 12B:
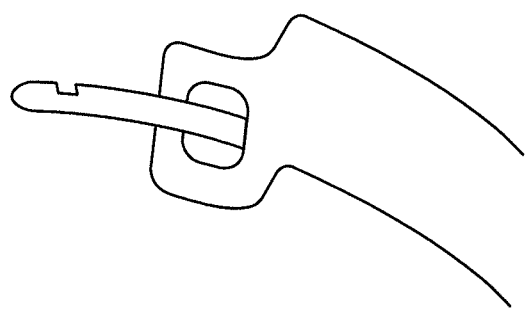
FIGS. 12B and 12C illustrate upper jaw members that are adapted at their distal ends to pull or change the direction of the bight after it has been pulled through the tissue.
Figure 12C:
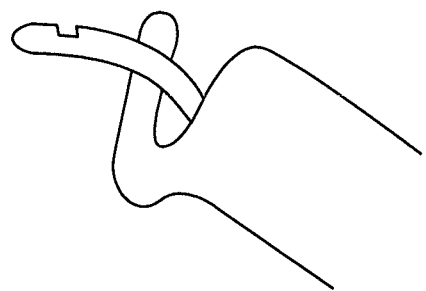

The orientation of the loop within the tissue may also be adjusted by the apparatus to make it easier to retrieve. For example, FIG. 12A illustrate a method of orienting the loop of a bight so that the loop is more easily accessible by a tool accessing the tissue from the same direction as the suture passer. In FIG. 12A, the suture is flipped from a distal (e.g., away from the entry point of the apparatus in the tissue) to a proximal (towards the entry point of the apparatus into the tissue) orientation. FIGS. 12B and 12C illustrate variations of apparatuses that are adapted to flip the suture bight proximally to make the bight easier to retrieve. When the upper jaw is retracted (after the needle has been retracted), the distal end of the upper jaw may pull on the suture bight and flip it proximally. For example, in FIG. 12B the upper jaw includes a large opening though which the tissue penetrator, and therefore the suture bight left behind upon removal of the tissue penetrator, passes. The loop (shown as a hook in FIG. 12C) pulls the bight distally before passing over the bight as the upper jaw is retracted proximally, similar to what is shown in FIG. 12A.

Figure 13:
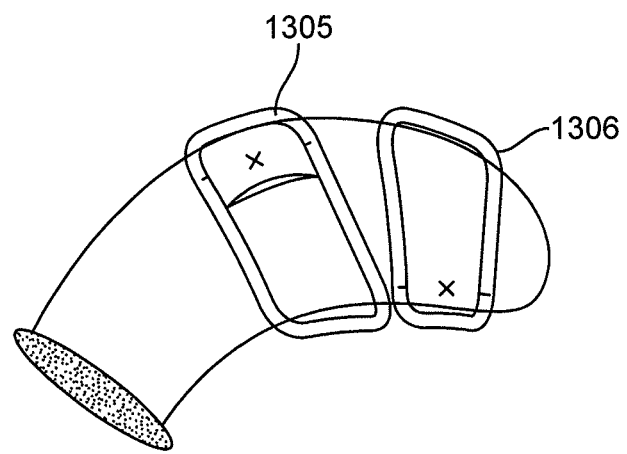
FIG. 13 illustrates the use of anchors or clamps to secure the tissue to be sutured (e.g., meniscus) so that the needle or suture passer does not shift or move the tissue undesirably during operation of the device.

Any of the variations described herein may be used with one or more anchors to hold or secure the target tissue relative to the apparatus when suturing. For example, in particular, when the suture passing apparatus is not adapted to clamp or hold of secure the portion of the tissue around the suture, the tissue (e.g., meniscus) may move when the needle begins to penetrate. This unintended movement may cause the needle to deflect/buckle, resulting in a misfire of the suture passer. In FIG. 13, temporary clamps 1305, 1306 are placed on the meniscus to fix the meniscus and prevent any motion of the meniscus. After placing the clamps the suture passing system can be introduced to pass suture. Another potential benefit of the clamp could be alignment markers, which are used to align the device to the clamp to facilitate precise targeting of the needle and suture passing. The clamps are then removed after the suture is placed. The clamps can also have mating features that facilitate docking of the suture passer to the clamp. This configuration of suture passer and temporary clamp could allow for suture positioning to be less sensitive to device or tissue movement during suture placement.

As mentioned above, any of the thin, sliding upper jaws may include a suture capture (e.g., "trap") that holds the suture in the upper jaw as the tissue penetrator is retracted proximally back into the lower jaw. FIGS. 14A-14C show one variation of an upper jaw having a suture capture formed by two layers of material. In FIG. 14A, a bottom view of the upper jaw shows the thin upper jaw having two layers. The top layer 1401 is solid and hard enough to deflect the needle away from condyle surfaces. The bottom layer 1403 is flexible and provides a spring force up against the top layer. In the bottom view of FIG. 14A, the bottom layer 1403 includes a window region 1407 for the tissue penetrator to pass through and then deflect off of the top layer 1401. The tissue penetrator and suture then penetrate between the distal tips of the two layers and travel beyond the distal tips. This is illustrated in FIG. 14B (showing the tissue penetrator 1414 between the two layers carrying a suture 1417). In FIG. 14C, when tissue penetrator is retracted, the spring force between the two layers grips and retains the suture 1417 bight beyond the tip of the upper jaw. Therefore, when the device is removed from the joint the suture bight is trapped by the upper jaw and is pulled from the tissue. To enhance the suture retainer, either of the layers could have teeth on them.

Figure 15:
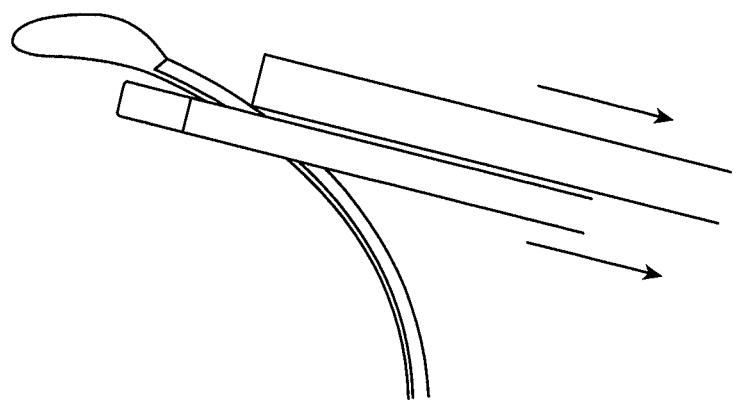
FIG. 15 shows a variation of the upper jaw of FIG. 14A-14C in which the leaflets forming the upper jaw may be moved laterally relative to each other to capture and/or release a loop of suture.

In another embodiment of FIG. 14A-14C, the upper jaw is retractable and as it is retracted, the lower layer of the upper jaw may retract farther than the top layer; as a consequence, the suture bight may be cinched between the two layers, trapping the suture and allowing the suture bight to be removed from the joint with the device. This is illustrated in FIG. 15.

Figure 16A:
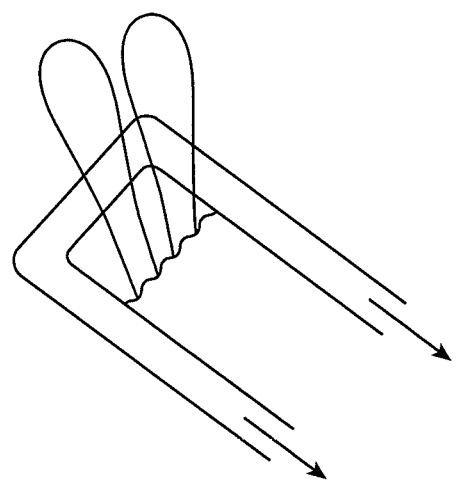
FIG. 16A shows another variation of an upper jaw including a loop or opening at the distal end that may capture or retain a bight of suture passed from the lower jaw.
Figure 17:
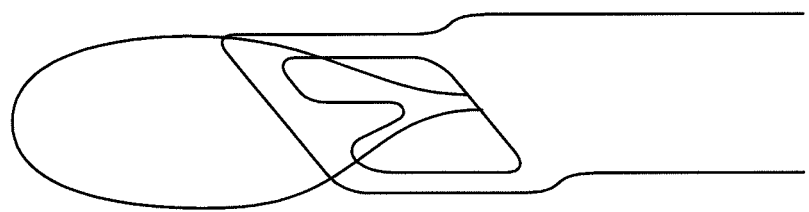
FIG. 17 illustrates another variation of the distal end of a suture passer apparatus having a suture retainer region at the upper jaw.

FIGS. 16A-16C illustrate another variation of an upper jaw having a suture retainer. In FIG. 16A-16C, the upper jaw includes two pieces that are in the same plane, to minimize thickness and the relative motion between the pieces. The outer piece 1601 cinches to the inner piece 1603 to cinch down on the suture. Alternatively, a one piece upper jaw with a window could be retracted into the shaft to "snare" the suture. A window in a one piece thin upper jaw may include snaring features that could assist in catching and holding onto the suture as the upper jaw is retracted into the shaft. In FIG. 17, the snare feature and window are slightly lower than the deflective surface of the upper jaw for the purpose of ensuring that the needle passes through the window.

FIG. 18 illustrates another variation of a suture retainer on the upper jaw. In FIG. 18, an upper jaw with a snaring feature 1803 also has a leaf spring region 1805 that deflects slightly when the needle hits it. This deflection helps to ensure that the needle and suture travel through the window and above the snaring feature.

Alternatively, in some variations the distal end of the upper jaw member may be adapted (e.g., by doubling back over itself) to form a compression region that may be displaced by the tissue penetrator, rather than requiring a separate layer. The very distal end region may include an opening or passage for the tissue penetrator to continue to extend distally past the distal end of the upper jaw, or distal movement of the tissue penetrator may be prevented by the bend formed in the upper jaw. FIGS. 19A-19B and 20A-10B illustrate variations of upper jaws that include a suture retainer formed by doubling the material forming the upper jaw back onto itself.

Figure 21:
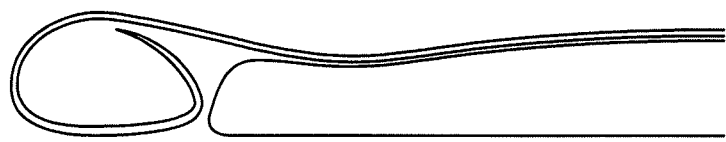
FIG. 21 shows another variation of an upper jaw including a suture retainer region.

In FIG. 19A, the distal end region forms a suture capture or "trap" in the thin upper jaw. The suture traps 1903, 2003 on the distal end provides a spring force to retain the suture from the tissue penetrator 1905, 2005. FIGS. 19A and 20A show alternate embodiments of spring mechanisms that could trap the suture onto the upper jaw when retracting the tissue penetrator. In FIGS. 19A-20B, these suture traps in the upper jaws have windows at the distal end to allow the needle to pass through the trap and leave a suture bight distal of the trap. FIG. 21 illustrates another variation of a suture capture (suture trap) that also clamps (or springs) down to nest over the lower jaw and create a smooth profile for inserting the device into the tissue.

Figure 22A:
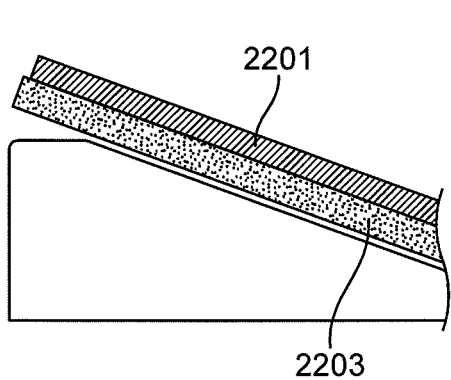
FIG. 22A shows another variation of an upper jaw including a suture retainer region configured as a soft material attached to a more rigid or hard material at the distal end of the upper jaw.
Figure 22C:
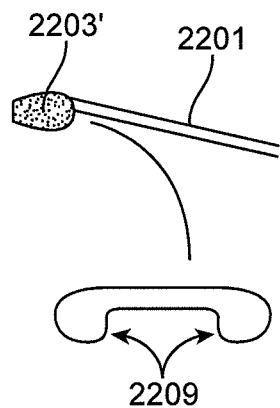
FIGS. 22B and 22C illustrate similar variations.
Figure 22B:
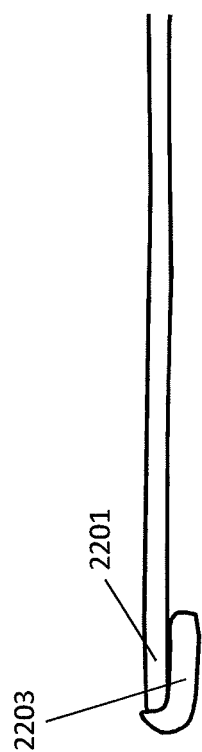

In some variations, the upper jaw includes a suture capture region that is formed of a material that can be penetrated by the tissue penetrator but that provides sufficient friction to retain the suture when the tissue penetrator is withdrawn from the upper jaw member. For example, FIG. 22A-22C illustrates a thin upper jaw with two layers, a hard upper layer 2201 that deflects the needle and a soft lower layer 2203 (for example, silicone) that the tissue penetrator (e.g., needle) can penetrate and travel through. When the needle is retracted, the soft lower layer would apply friction to the suture to retain the suture bight in the upper jaw. FIG. 22B shows a variation including the soft material 2203 just at or near the distal end of the device; the material may provide a soft and/or slippery surface to prevent damage to the tissue into which the upper jaw is inserted. In FIG. 23C, the soft material 2203' (for example, silicone) forming part of the suture trap at the end of the upper jaw is intended to be penetrated by the tissue penetrator that can pass through the soft material forming the suture trap, and when the needle retracts, the suture bight is retained in the suture trap. The cross section of the upper jaw (shown in the inset of FIG. 22C) could have rails 2209 on the side to guide the tissue penetrator into the suture capture trap.

FIG. 23 illustrates another variation of a suture capture that is formed by a soft material. In the upper jaw of FIG. 23, there are two layers, a hard upper layer 2301 and soft lower layer 2305. However, in this embodiment the hard upper layer 2301 deflects slightly when the tissue penetrator 2307 hits it, encouraging the tissue penetrator to pass between the two layers. When the needle retracts, the pinch force between the hard and soft layer retains the suture in the upper jaw.

FIG. 24A illustrates two concepts for upper jaws including suture capture. In both concepts, the upper jaw/needle combination deflects the needle proximally. In the first concept, a second deflecting feature is intended to deflect the needle back down to the lower jaw where a suture tray may exist. In the second concept, the needle continues to travel proximally toward the upper jaw hinge region where a suture trap exists.

In FIG. 24B, similar to that shown in FIG. 24A, a tissue penetrator that is deflected proximally and back down to the lower jaw picks up suture in the lower jaw. This concept could result in a continuous suture passer. With one pass, the tissue penetrator drops off the suture in the lower jaw, and a second tissue penetrator pass can then pick up the suture, etc.

Figure 25:
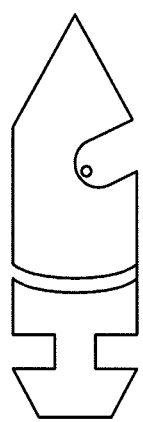
FIG. 25 shows one variation of a needle and pusher that may be used.

As mentioned above, any of the apparatuses described herein may be used with any appropriate tissue penetrator (e.g., needle). In general, the tissue penetrator may be an elongate, thin and sharp (at the distal end) apparatus that is adapted to pass a suture, and may include a suture retainer region, such as an eyelet, hook, clamp, etc. In general, a tissue penetrator is coupled at the proximal end within the lower jaw so that it can be extended and retracted, e.g., by pushing/pulling on the proximal end. FIG. 25 illustrates one variation of a tissue penetrator that is shuttled between the lower and upper jaw. The tissue penetrator has features on the proximal end that allow the lower jaw to release the tissue penetrator so that the tissue penetrator and suture can dock in the upper jaw.

Figure 26A:
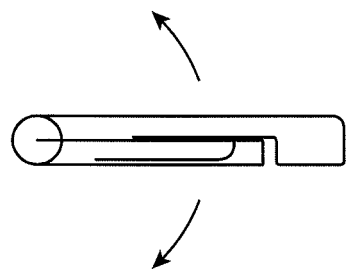
FIGS. 26A and 26B illustrate variation of suture passers having a distal end region that includes a bendable upper and bendable lower jaw.
Figure 26B:
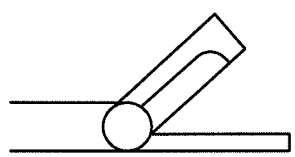

FIGS. 26A and 26B illustrate examples of upper and lower jaws that articulate to allow the suture passer to conform to the anatomy that suture passer is operating in. Thus, in these examples, both the upper and lower jaws may pivot relative to the elongate body to change the angle.

Figure 27:
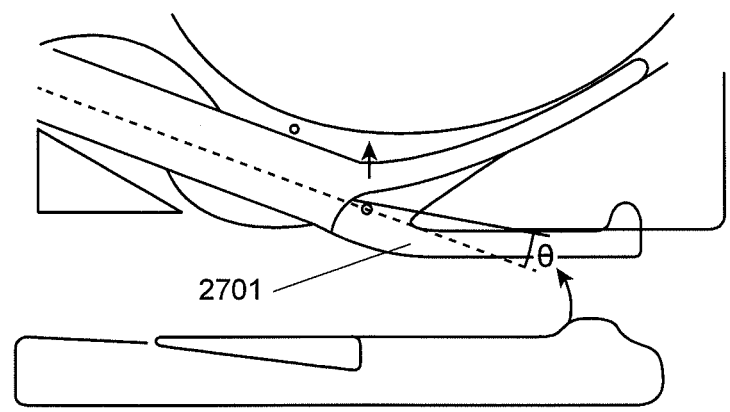
FIG. 27 illustrates the operation of a suture passer apparatus having a bendable lower jaw.
Figure 28:
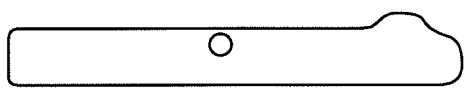
FIG. 28 illustrates the articulating attachment of a jaw member for use with a bending lower and/or upper jaw member.

In FIG. 27, the lower jaw is adapted to pivot (e.g., upwards). This may be advantageous in the confines of the knee when accessing a meniscus, since the shaft is often entering the joint at an angle to get above the anterior portion of the meniscus. Thus, a pivoting lower jaw may provide easier access in tight joints. The lower jaw 2701 in FIG. 27 may be adapted for use in a suture passer such as the variation shown in FIGS. 36A-36B, having a sliding lower jaw member housing a tissue penetrator and a pivoting upper jaw. The tapered lower jaw may be adapted to slide within a keyway in the shaft to allow the lower jaw to advance/retract in addition to pivoting upwards. FIG. 27 demonstrates how having a lower jaw with an upwardly bent angle or hinge may be beneficial in placing the distal end of the suture passer when the access portal into the joint must be placed above the anterior horn of the same meniscus to be repaired. The portal above the meniscus may force an approach vector that is pointing downward at the tibial plateau. However, when the lower jaw is placed inferior to the meniscus, it may be easier to get it in place if the lower jaw traverses parallel with the tibial plateau. In FIG. 28, a lower jaw could advance/retract and pivot in an upwardly (or downwardly) curved shaft where the keyway is also curved.

Figure 29:
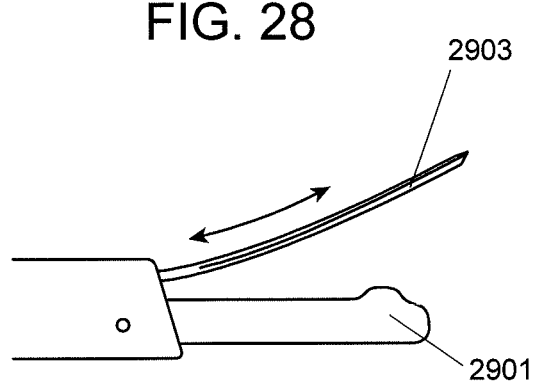
FIG. 29 show a hinged lower jaw and an upper jaw that may be axially slid (extended and/or retracted); the lower jaw may be clamped to secure the tissue between the upper and lower jaws, preventing sliding or misfiring of the tissue penetrator.

FIG. 29 illustrates a side view of a device with a very thin, extendable/retractable upper jaw with a lower jaw that clamps. Thus, the lower jaw may house the sliding tissue penetrator but may also be adapted to pivot and therefore clamp tissue between the upper 2903 and lower jaws 2901. The upper jaw may be similar to the upper jaws shown in FIGS. 1B-1E (e.g., may be thin and configured to deflect the tissue penetrator). In addition to improved access, the clamping lower jaw 2901 feature may mitigate the challenge of the movement of meniscus as the tissue penetrator begins to penetrate the meniscus. The clamping mechanism could be facilitated by tensioning a cable or a linkage.

Figure 30:
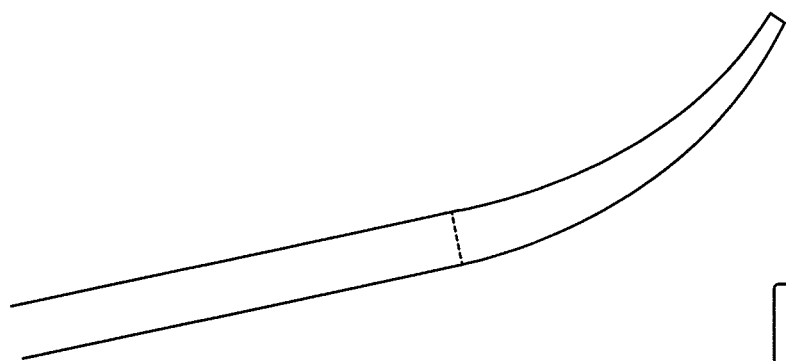
FIG. 30 is a side view that illustrates another variation of an upper jaw having a rigid or semi-rigid region more proximal to a flexible (and narrower) distal region. The distal region is also curved relative to the straighter, flatter more proximal region.

Another variation of the configuration for the upper jaw is shown in FIG. 30. In this example, the upper jaw may be configured as a clamping upper jaw (e.g., see the variation shown in FIGS. 36A-36B) with a rigid section and a flexible section. Both sections may have hard elements on the inferior surface that could deflect the needle away from non-target (e.g., condyle surfaces). The rigid section may provide a clamping region of the upper jaw. The end of the rigid section may correspond with the end of the tooth on the lower jaw to maximize the effectiveness of the clamp. The inferior surface of the clamping region may be straight to maximize clamp effectiveness and the superior surface is curved to maximize access. The flexible section may be thin and flexible to conform to the anatomy and maximize access. The flexible section may also be coated with a soft material to facilitate atraumatic insertion between the femoral condyle and the meniscus.

Figure 31:
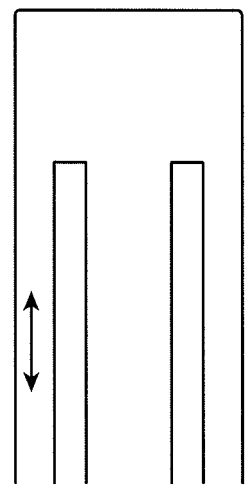
FIG. 31 shows a top view of another variation of an upper jaw having a pair of tensioning region that may be used to curve the upper jaw, e.g., by pulling or pushing on the tensioning members.

In general, the upper jaws for a suture passer apparatus may be adapted to bend or flex, as mentioned. In some variations this bending or flexing may be controlled. For example, FIG. 31 illustrates the distal end region of one variation of an upper jaw member (deflector jaw). In FIG. 31 the upper jaw is a one piece, very thin upper jaw (shown in a top view). The central strut of the upper jaw is fixed at the proximal end (e.g., at the bottom in FIG. 31). When the two outer struts are pulled in tension, the central strut bows upward, providing a downward clamp force for the upper jaw. When the two outer struts are compressed, they bow downwards and the upper jaw lifts upwards. This variation may be included as part of a sliding upper jaw or as part of a pivoting upper jaw.

Figure 32A:
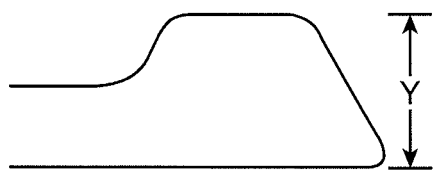
FIGS. 32A and 32B show a side view and top view, respectively, of a distal end of a lower jaw member that is particularly thin (width, x), particularly as compared to the height (y), e.g., heath is more than 1.5× width, more than 2× width, more than 2.5× width, etc.).
Figure 32B:
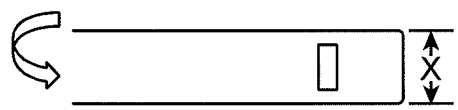
Figure 32C:
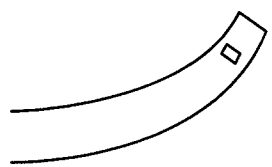
FIG. 32C illustrates a curved variation, in which the tip is curved or bent to the left or right.

FIGS. 32A and 32B illustrate variations of the lower jaw that may be used. In FIGS. 32A and 32B, the narrow width lower jaw (compared to the height) may be particularly useful in variations of suture passers such as those shown in FIGS. 1B-1E. In FIGS. 32A and 32B, the lower jaw with a narrow width and a height necessary to eject the tissue penetrator along the desired trajectory path. The advantage of the narrow width is that it allows the user to gain access in tight joints by rotating the device sideways. Once the device is in position, the device can be rotated back to fire the needle through the meniscus. FIG. 32C shows another embodiment of the above concept, in which the lower jaw is curved to one side, as shown. When a device having a curved lower jaw is rotated sideways for insertion, there is an upward bend to allow for easier access. Once the device is in position, the device can be rotated back to fire the tissue penetrator through the tissue. In variations having an upper jaw, the upper jaw may be curved in a complimentary direction.

Figure 33:
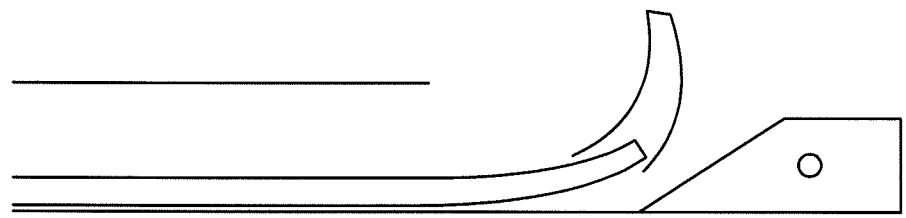
FIG. 33 illustrates another variation of a suture passer in which the lower jaw include a tissue penetrator that is not deflected out of the lower jaw by extending axially (e.g., sliding) or not exclusively extended by sliding, but is (at least in part) extended by pushing the distal region of the tissue penetrator without sliding (e.g., by pulling a deflector proximally).

As discussed above, in general, the tissue penetrator is adapted to extend from the lower jaw by sliding the tissue penetrator distally. However in some variations the lower jaw may extend the tissue penetrator by instead driving a deflection member proximally or distally to push the tissue penetrator. For example, in FIG. 33, a lower jaw may be made relatively thin (in height) as it does not require a passive needle channel that directs the needle vertically, but instead a cam may be actuated (e.g., pulled proximally) to bend a metal sheet/strip to actively form the tissue penetrator channel that will direct the tissue penetrator vertically.

In any of the suture passer variations described herein, the jaws (lower/upper, first/second, etc.) may be arranged in reverse (e.g., the "upper" jaw may be positioned in a "lower jaw" position and vice versa.

Figure 34:
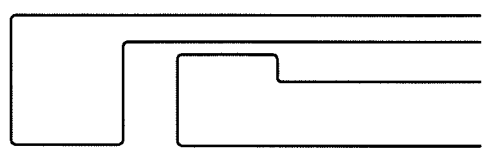
FIG. 34 shows one variation of a section through a distal end of a suture passer having an upper and a lower jaw in which the lower and upper jaws nest together to allow a relatively narrow profile.
Figure 35:
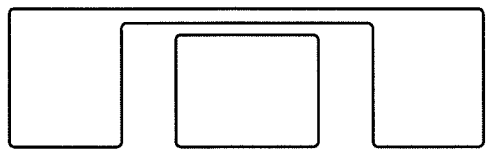
FIG. 35 shows another variation of a section through a distal end of a suture passer having a distal including an upper jaw nested with a lower jaw.

The overall distal end of the device may be adapted to be narrower or thinner by nesting the upper and lower jaws. For example, FIG. 34 illustrates nesting the upper and lower jaw together to create a low profile for entering the joint space. Similarly, FIG. 35 illustrates another nesting concept to create a low profile for entering the joint space. The lower jaw is in the center; the upper jaw is the outer feature.

Figure 36A:
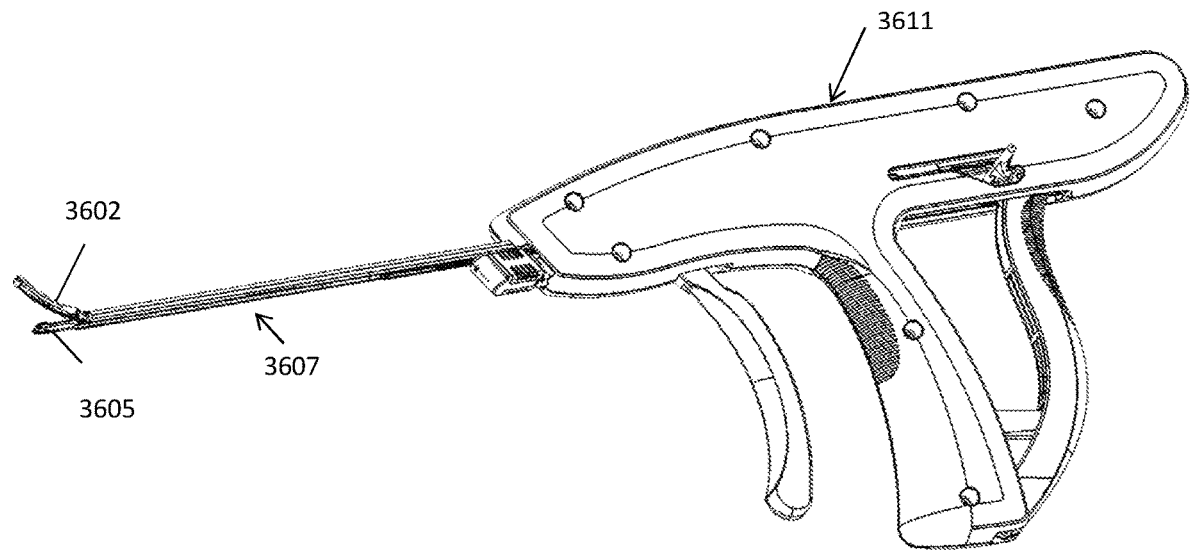
FIG. 36A shows a side perspective view of a suture passer device having a distal end with a sliding lower jaw and a bendable (pivot able) upper jaw; a tissue penetrator may be housed within the lower jaw (which in this variation is adapted as a pre-loaded suture containing cartridge) and may be extended from the lower jaw to the upper jaw, where it is again deflected distally to pass a bight of suture to the upper jaw.
Figure 36B:
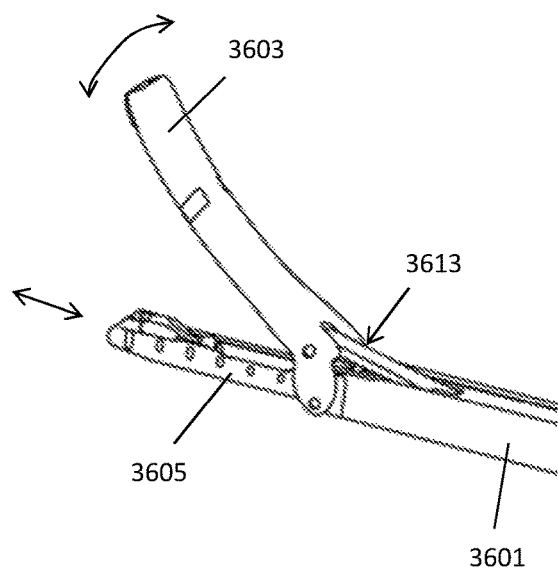
FIG. 36B is an enlarged view of the distal end of the device with the upper jaw bent away from the long distal-to-proximal axis of the device and the lower jaw extended distally.

FIGS. 36A and 36B illustrate a suture passer apparatus such as the variation described in US 2012/0283753, US 2013/0331865, and PCT/US2014/030137 each of which is herein incorporated by reference in its entirety. In FIG. 36A, for example, the distal end of the suture passer apparatus includes a hinged, pivoting upper jaw 3602 that pivots relative to the elongate body 3607. A sliding lower jaw 3605 houses a tissue penetrator (not visible in FIG. 36A or FIG. 36B) that can be extended laterally across the distal-facing opening formed by the upper 3602 and lower 3605 jaws when they are extended. The proximal handle 3611 includes multiple controls for controlling the motion of the upper jaw, the lower jaw and the tissue penetrator. In this example, the lower jaw is pre-loaded as a cartridge with suture. Any of the apparatus variations described herein may be adapted to include pre-loaded suture, including variations in which the lower jaw is fixed, pre-bent, and/or slidable.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A suture passer apparatus, the apparatus comprising:
    an elongate body having a proximal end connected to a proximal handle and a distal end,
    wherein the elongate body extends in a long axis;
    a lower jaw member axially fixed to the distal end of the elongate body such that the lower jaw member extends distally of the distal end of the elongate body;
    an upper jaw member configured to move axially between a retracted position in which the upper jaw member is entirely within the elongate body and an extended position in which the upper jaw member is extended distally out of the distal end of the elongate body, wherein at least a portion along a length of the upper jaw member includes a strip of metal defining a region that is biased to bend and curve away from the long axis of the elongate body as it is extended out of the distal end of the elongate body; and
    a tissue penetrator housed within the lower jaw member and configured to slide distally within the lower jaw member and extend laterally from the lower jaw member to carry a suture from the lower jaw member, the tissue penetrator configured to be deflected against the upper jaw member to extend distally or proximally.

2. The apparatus of claim 1, wherein the upper jaw member comprises a suture capture to hold the suture on the upper jaw member after the tissue penetrator is deflected against the upper jaw member.

3. The apparatus of claim 1, wherein the strip of metal defines a bottom surface that the tissue penetrator is deflected against when the tissue penetrator is deflected against the upper jaw member.

4. The apparatus of claim 1, wherein the lower jaw member comprises a deflection surface within the lower jaw member to deflect the tissue penetrator laterally out of the lower jaw member when the tissue penetrator is extended distally in a direction of the long axis.

5. The apparatus of claim 1, wherein the lower jaw member is bent or curved relative to the long axis.

6. The apparatus of claim 1, wherein the lower jaw member has a width that is less than a thickness of the lower jaw member.

7. The apparatus of claim 1, wherein the strip of metal defines a bottom surface having a tissue engaging surface.

8. The apparatus of claim 1, wherein the upper jaw member is formed of a shape memory material.

9. A method of suturing tissue, the method comprising:
    positioning a first jaw of a suture passer adjacent a target tissue, wherein the first jaw of the suture passer is axially fixed to a distal end of an elongate body of the suture passer such that the first jaw extends distally of the distal end of the elongate body;
    sliding a second jaw of the suture passer distally from a retracted position in which the second jaw is entirely within the elongate body an extended position in which the second jaw extends distally out of the elongate body after positioning the first jaw adjacent the target tissue to position the target tissue between the first jaw and the second jaw, wherein at least a portion of a length of the second jaw comprises a strip of metal defining a region that is biased to bend and curve away from the first jaw as it is extended distally from the elongate body;
    passing a suture from the first jaw to the second jaw by laterally extending a tissue penetrator from the first jaw, though the target tissue, and deflecting a tip of the tissue penetrator from the second jaw distally or proximally, wherein the suture is carried by the tissue penetrator.

10. The method of claim 9, further comprising securing the suture on a suture capture of the second jaw.

11. The method of claim 9, wherein the deflecting comprises deflecting the tip of the tissue penetrator the tip of the tissue penetrator by a bottom surface of the strip of metal.

* * * * *